(12) United States Patent
Kletskin

(10) Patent No.: US 6,246,903 B1
(45) Date of Patent: Jun. 12, 2001

(54) STATISTICAL MAPPING OF THE PHYSIOLOGICAL STATE OF THE HEART OF A MAMMAL

(75) Inventor: Solomon Kletskin, Ma'ale Adumim (IL)

(73) Assignee: Cardiosol Ltd., Yokneam (IL)

( * ) Notice: Subject to any disclaimer, the term of this patent is extended or adjusted under 35 U.S.C. 154(b) by 0 days.

(21) Appl. No.: 09/308,374

(22) PCT Filed: Nov. 10, 1997

(86) PCT No.: PCT/IL97/00362

§ 371 Date: Jul. 2, 1999

§ 102(e) Date: Jul. 2, 1999

(87) PCT Pub. No.: WO98/22791

PCT Pub. Date: May 28, 1998

(30) Foreign Application Priority Data

Nov. 15, 1996 (IL) ........................................ 119622

(51) Int. Cl.[7] ................................................. A61B 5/045
(52) U.S. Cl. ................................................. 600/509
(58) Field of Search ..................................... 600/509, 517, 600/518, 515

(56) References Cited

U.S. PATENT DOCUMENTS

| | | | |
|---|---|---|---|
| 4,527,240 | 7/1985 | Kvitash | 364/413 |
| 5,092,341 | 3/1992 | Kelen | 128/702 |
| 5,188,116 | 2/1993 | Pommrehn et al. | 128/696 |
| 5,419,338 | 5/1995 | Sarma et al. | 128/703 |

*Primary Examiner*—Scott M. Getzow
(74) *Attorney, Agent, or Firm*—Fitch, Even, Tabin & Flannery

(57) ABSTRACT

Providing an indication of the physiological state of the heart of a mammal by the steps of detecting periodic activity of internal heart organs in a sequence of heart cycles; observing a predetermined physical quantity characteristic of a selected activity; evaluating predetermined statistical parameters of the predetermined physical quantity for a selected number of the sequence of heart cycles; and comparing the evaluated statistical parameters with reference values thereby to provide an indication of the state of the selected activity.

37 Claims, 22 Drawing Sheets

STATISTICAL MAPPING OF THE PHYSIOLOGICAL STATE OF THE HEART OF A MAMMAL

FIELD OF THE INVENTION

The present invention relates to electrocardiography in general and, in particular, to variability evaluation of electrocardiograms.

BACKGROUND OF THE INVENTION

An electrocardiogram, or "ECG", is a graphical record of the electric potentials produced by activity of the heart. In the same way that heart activity is cyclical, the electrical potentials produced by activity of the heart are also cyclical, and measurement thereof has resulted in the well known characteristic ECG waveform. It is known that the portions of this waveform correspond to different events which together form the cyclical activity of the heart, and the known, basic P, Q, R, S, T, U waves are so-called, due to six commonly identified transition points on an ECG waveform; portions of the waveform bounded by these points being understood as representing activities of specific intra-heart organs. By way of example, the QRS portion (i.e. that portion of the waveform defined between the QRS nodes), known also as the QRS complex, occurs at the time that the ventricles of the heart contract, or "systole." The so-called "T wave" is caused by repolarization of the electrical system following contraction, or "diastole." It is understood that changes observed in any of these waves can be used for various cardio-diagnostic purposes, by way of example, the S-T elevation is taken as one of the classic signs of heart infarction.

It is, in fact, known that current interpretation of the electrocardiogram is very limited, due to the fact that the heart is known to be a very complex organ, and each operating cycle thereof is not limited merely to a small number of events, such as the electrocardiogram might indicate. The occurrence of this very large number of heart events is well known, and, by way of example, is discussed in a book entitled *CLINICAL SCALAR ELECTROCARDIOGRAPHY*, by Lipman, Massie and Kleiger; and bearing Library of Congress Catalog Card Number 72-188577.

It is further known to extract useful information concerning certain heart organ functions by assessing variability of data contained therein. An indication of the state of the art is provided by U.S. Pat. No. 5,188,116 and 5,419,338.

The '116 publication, entitled "Electrocardiographic Method and Device," is directed to method and apparatus for detecting heart disease from an electrocardiogram (ECG). The method comprises the steps of acquiring the ECG signals, correcting for signal variability caused by breathing and calculating the level of remaining variability due to myocardial function. The apparatus comprises a signal input system, a storage system, a microprocessor and an output system. The microprocessor has program logic for processing signal data in accordance with the method The '338 publication, entitled "Autonomic Nervous System Testing by Bi-Variate Spectral Analysis of Heart Period and QT Interval Variability," discloses apparatus and a method for testing the autonomic nervous system of a mammal through bi-variate analysis of heart Period (RR) and QT interval variability obtained through data processing of electrocardiographic data. The method and apparatus enable both the parasympathetic and sympathetic controls on the heart to be evaluated for imbalances therebetween, which may indicate a predisposition for sudden cardiac death.

Neither of the above methods provides an overall approach which enables the determination of the overall state of the heart of a subject relative to a norm, the mapping of various heart functions, and the determination of a trend, such that even if a subject is seen to have a serious heart condition, it is possible to establish whether his condition is improving or deteriorating.

SUMMARY OF THE INVENTION

It is thus an aim of the present invention to provide a novel method and a device for the measurement of heart activity and in-depth quantitative prognostic evaluation of the results of the ECG. The method and device are based on high resolution sampling of ECG readings, accurate establishment of multiple characteristic points, statistical evaluation of the intervals, and mapping of the evaluated data.

There is thus provided, in accordance with a preferred embodiment of the invention, a method of providing an indication of the physiological state of the heart of a mammal by the steps of detecting periodic activity of internal heart organs in a sequence of heart cycles; observing a predetermined physical quantity characteristic of a selected activity; evaluating predetermined statistical parameters of the predetermined physical quantity for a selected number of the sequence of heart cycles; and comparing the evaluated statistical parameters with reference values thereby to provide an indication of the state of the selected activity.

Additionally in accordance with a preferred embodiment of the invention, the step of observing includes the step of measuring the time period taken by each activity, and the step of evaluating includes the step of evaluating predetermined statistical parameters of the time periods of a selected activity in a selected number of the sequence of heart cycles.

Further in accordance with a preferred embodiment of the invention the step of evaluating includes evaluating a first statistical parameter indicating the state of the selected activity at the time of performing the step of detecting, and the step of comparing includes comparing the evaluated first parameter with a reference range, and further includes the step of determining a relationship between the evaluated first statistical parameter and the reference range, thereby to also determine the physiological state of the mammal at the time of performing the step of detecting.

Additionally in accordance with a preferred embodiment of the invention, the step of evaluating also includes evaluating a second statistical parameter indicating a trend in the state of the selected activity, and the step of comparing also includes comparing the evaluated second parameter with a reference range, and further includes the step of determining a relationship between the evaluated second statistical parameter and the reference range, thereby to also determine the trend in the state of the selected activity.

Further in accordance with a preferred embodiment of the invention the step of comparing further includes the step of providing a visual reference system which includes first visual indications corresponding to the reference range, including a plurality of reference axes, each corresponding to a different predetermined heart activity, and the step of determining a relationship includes the sub-steps of:

providing on the reference axes second visual indications corresponding to values of a predetermined statistical quantity for each heart activity; and visually comparing the second visual indications with the first visual indications, thereby to determine a relationship therebetween.

Additionally in accordance with a preferred embodiment of the invention, the reference system is a multi-axis reference system which has a plurality of axes radiating from an origin, wherein each axis defines a scale on which is indicated a range of possible values of the predetermined statistical quantities corresponding for a predetermined heart activity, and wherein the first visual indications of the reference system are closed-shape line markings provided concentrically about the origin, thereby to define two or more reference regions, wherein visual indications within a first region indicate a first state of health of the heart of the mammal, and visual indications within a second region indicate a second state of health of the heart of the mammal, different from the first state of health, and the step of comparing the second visual indications with the first visual indications includes determining where the second visual indications fall relative to the reference regions, thereby to visually determine the state of health of the heart of the mammal.

Further in accordance with a preferred embodiment of the invention the step of providing a reference system includes the steps of detecting periodic activity of internal heart organs in a sequence of heart cycles for a statistically representative number of subjects each having a similar physiological condition; observing a plurality of predetermined physical quantities each characteristic of a known heart activity; evaluating selected statistical parameters of each of the predetermined physical quantities for a selected number of the sequence of heart cycles for each of the subjects; determining minimum and maximum values for each of the selected statistical parameters, thereby to define a range of values for each parameter for subjects having the physiological condition; and plotting the range of values on the multi-axis reference system, thereby to indicate visually the minimum and maximum values for each statistical parameter for each heart activity.

Additionally in accordance with a preferred embodiment of the invention, the step of detecting periodic activity of internal heart organs includes sensing at the body surface of a mammal electrical potentials produced by heart activity thereof, during a predetermined minimum number of consecutive heart cycles; providing an analog output signal corresponding to the sensed electrical potentials; sampling the analog output signal at a high frequency sampling rate, so as to convert the analog output signal into digital signals which retain substantially all the information contained in the sensed electrical potentials; storing the digital signals as input data in an initial input file; and providing a high resolution output waveform corresponding to the input data in which substantially only information concerning heart activity is represented.

The step of providing a high resolution waveform includes determining waveform characteristic points, superposing the characteristic points on the output waveform, thereby to divide the waveform into a plurality of waveform cycles each corresponding to a single heart cycle, and so also as to divide each waveform cycle into a plurality of waveform portions each being located between two selected characteristic points, and being defined by a plurality of points; selecting a waveform portion alignment point; aligning with each other all corresponding portions of the waveform cycles along the selected alignment point; and averaging the ordinates of all the points of all the aligned waveform portions, thereby to reduce the effects of non-useful information and thus to produce a single waveform which is characteristic of the heart activity of the mammal.

In accordance with a further embodiment of the invention, there is provided a system for providing an indication of the physiological state of the heart of a mammal, which includes apparatus for detecting periodic activity of internal heart organs in a sequence of heart cycles and for providing output signals corresponding thereto; apparatus, associated with the apparatus for detecting, for receiving the output signals and for determining in accordance therewith a predetermined physical quantity characteristic of an activity; apparatus for evaluating predetermined statistical parameters of the predetermined physical quantity for a selected number of the sequence of heart cycles; and apparatus for comparing the evaluated statistical parameters with reference values thereby to provide an indication of the state of the selected activity.

In accordance with yet a further embodiment of the invention, there is provided a multi-axis visual reference system for indicating the state of health of the heart of a mammal, which includes a plurality of axes radiating from an origin, wherein each axis defines a scale on which is indicated a range of possible values of a predetermined statistical quantity corresponding to a predetermined heart activity, and a plurality of closed-shape line markings provided concentrically about the origin, thereby to define two or more first and second reference regions, wherein visual indications within a first region indicate a first state of health of the heart of the mammal, and visual indications within a second region indicate a second state of health of the heart of the mammal, different from the first state of health.

Additionally in accordance with a preferred embodiment of the invention, the first region indicates a first range of values defining a statistically determined healthy range for the predetermined heart activity, and the second region indicates a second range of values beyond the first range, thereby to indicate an unhealthy range vis-a-vis the predetermined heart activity.

Further in accordance with a preferred embodiment of the invention the reference system also has a third region which indicates a third range of values defining a statistically determined diseased range for the predetermined heart activity, wherein the second region indicates a range of values between the first and third ranges, thereby to indicate a statistically determined intermediate health range for the predetermined heart activity.

Additionally in accordance with a preferred embodiment of the invention, the visual indications within the two or more reference regions correspond to the state of health of the heart of the mammal at the time at which heart activity of the mammal is sampled.

Further in accordance with a preferred embodiment of the invention the visual indications within the two or more reference regions correspond to a statistical determined trend in the state of health of the heart of the mammal subsequent to the time at which heart activity of the mammal is sampled.

BRIEF DESCRIPTION OF THE DRAWINGS

The present invention will be more fully understood and appreciated from the following detailed description, taken in conjunction with the drawings, in which.

DETAILED DESCRIPTION OF THE INVENTION

As will be appreciated from the following detailed description, the method of the present invention may be used to provide any of the following:

1. detection of functional deterioration of the heart at the pre-clinical stage;
2. detection of small abnormalities as well as small but persistent changes in the electrocardiographic waveform;
3. provision of a three-dimensional comparative visualization of the user-selected ECG waveform interval in the consecutive cycles for easy real-time dynamic appraisal of cardiac activity and hazardous cardiac state detection.

Figure 1A:
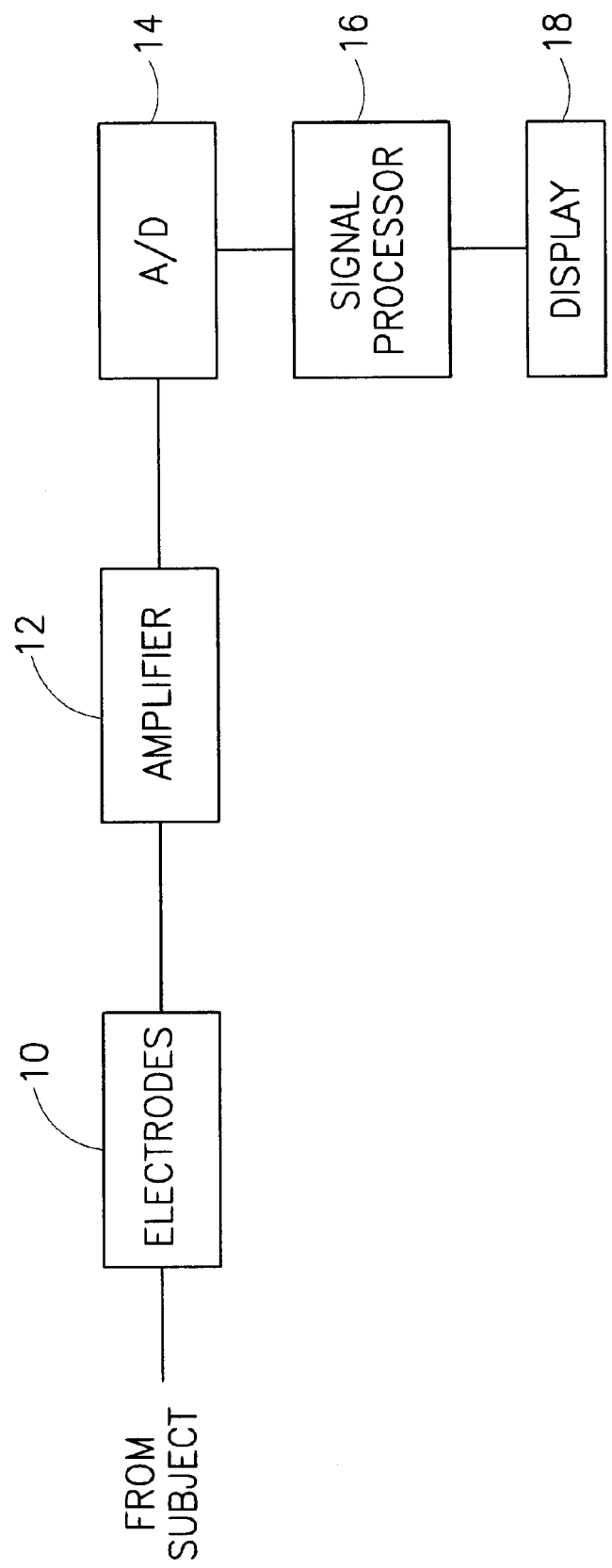
FIG. 1A is a block diagram illustration showing a device for performing electrical heart signal processing in accordance with the present invention
Figure 1B:
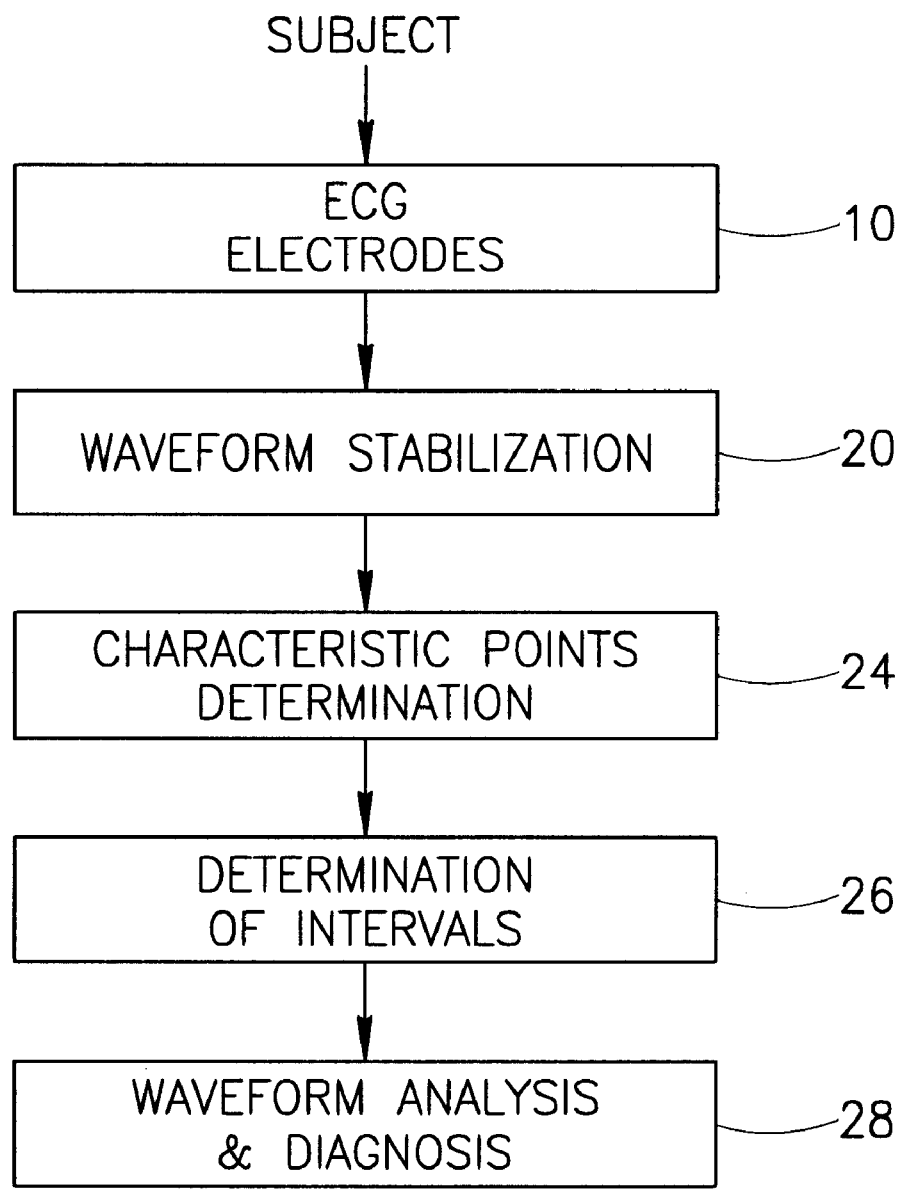
FIG. 1B is a flow chart showing the main stages of electrical heart signal processing in accordance with the present invention.

Referring to FIGS. 1A and 1B, the present invention provides an improved method of determining heart activity in a mammal. The method of the invention is based on employing electrodes 10 to sense at the body surface of a subject electrical potentials produced by heart activity thereof, during a predetermined minimum number of consecutive heart cycles. Output signals provided by electrodes 10 are amplified, as shown at 12, and are provided as analog output corresponding to the sensed electrical potentials, to an analog-to-digital converter 14.

Converter 14 is employed so as to sample the analog signals at a high frequency sampling rate, so as to convert the analog output signals into digital signals which retain substantially all the information contained in the sensed electrical potentials. Preferably the sampling is performed at a rate of greater than 500 times per second. A preferred minimum sampling rate is approximately 750 times per second, which as seen at waveform 42 in FIG. 4B, providing indications of phenomena not discernible on a conventional ECG operating at a sampling rate of 300–400 times per second. Most preferred, however, is a sampling rate of 5,290 times per second, or greater. The results shown and described herein are based mainly on this very high sampling rate, which reveals many different phenomena not previously discernible by electrocardiogram techniques.

It will be appreciated that, notwithstanding the prior art reluctance to use the analog data directly from the electrodes, this data contains a large amount of useful information about heart activity. The importance of using this 'raw' data lies in the fact that an extremely high sampling rate may be employed, as described, thereby providing very high resolution. This high resolution output enables focus on and magnification of selected portions of the ECG waveform which provide detail never before discernible by the human eye.

The digital data resulting from the above sampling, and which retains all detected information relating to heart activity, is stored on any suitable non-volatile storage medium, as an initial input file. A copy of the initial input file is made, and various processing techniques are performed thereon by suitable signal processing means 16, which is operative to provide a representative waveform cycle, a portion thereof, or subwaveforms thereof, as selected, on a suitable display 18, in accordance with the present invention.

Figure 2:
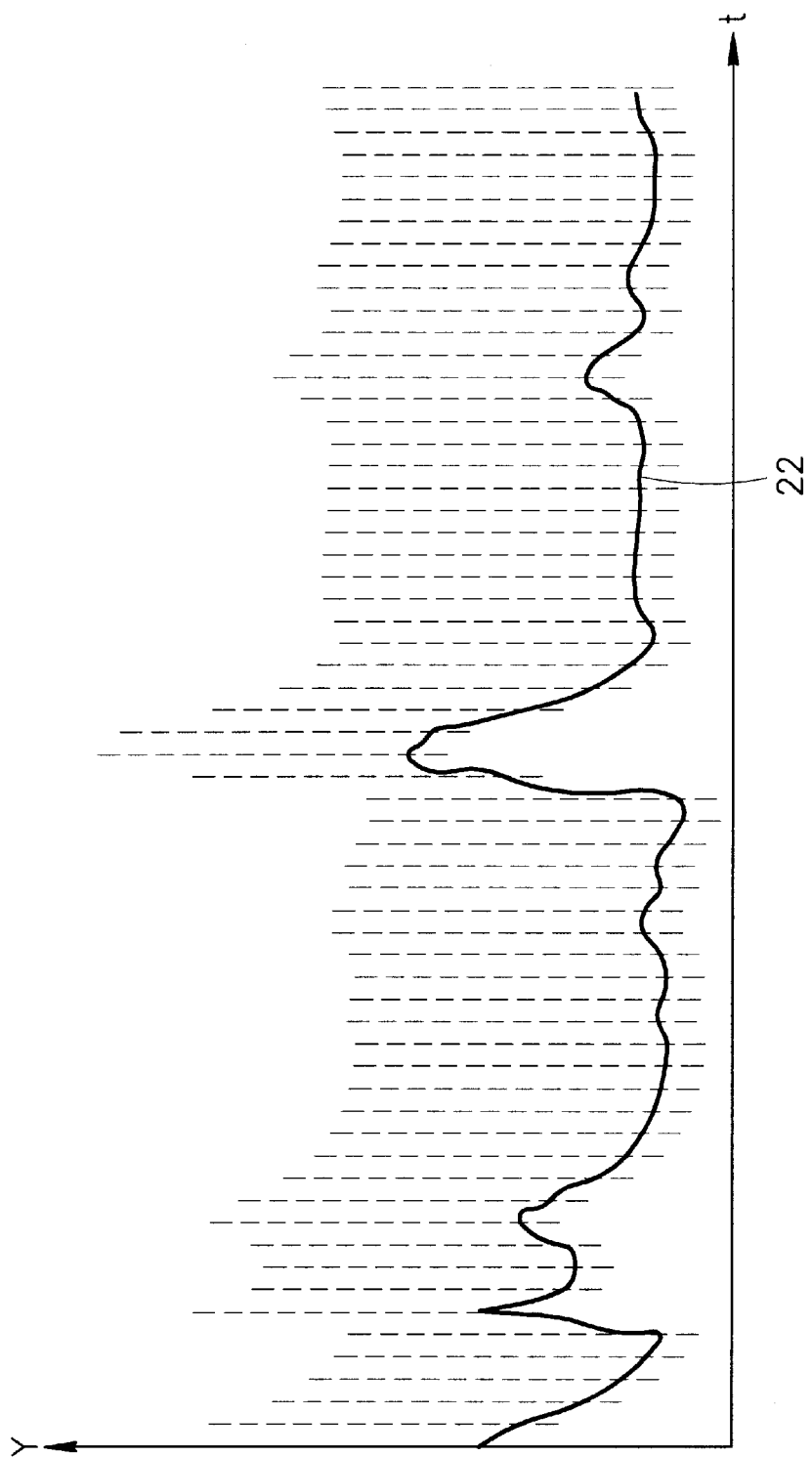
FIG. 2 is a compressed representation of a waveform including 100 consecutive ECG cycles, showing the baseline fluctuation thereof.

As shown in block 20 (FIG. 1B), a prerequisite for any meaningful analysis of the detected data is stabilization of the initial waveform. As seen clearly in FIG. 2, which is an actual ECG waveform of 100 consecutive heart cycles, the baseline of the waveform, shown as a solid line 22, is itself subject to substantial wander or fluctuation, such that it is necessary to stabilize the waveform so as to eliminate the wander and thereby provide a stabilized waveform which displays useful information. While prior art provides for stabilization of the waveform by electronic filtering which, as described above, causes substantial loss of much useful information, the present invention employs a technique of waveform stabilization which retains substantially all useful information by a process of high pass adaptive software filtering. This process is described in detail hereinbelow, in conjunction with FIGS. 3A–3C.

As seen in FIG. 1B, after the waveform has been stabilized (block 20), and a master file has been created containing the stabilized waveform, various additional techniques are applied thereto in order to make available much information that was previously lost in prior art ECG techniques. These subsequent steps include the determination of waveform characteristic points, (block 24), determination of intervals (block 26), and waveform analysis and diagnosis (block 2B).

Figure 3A:
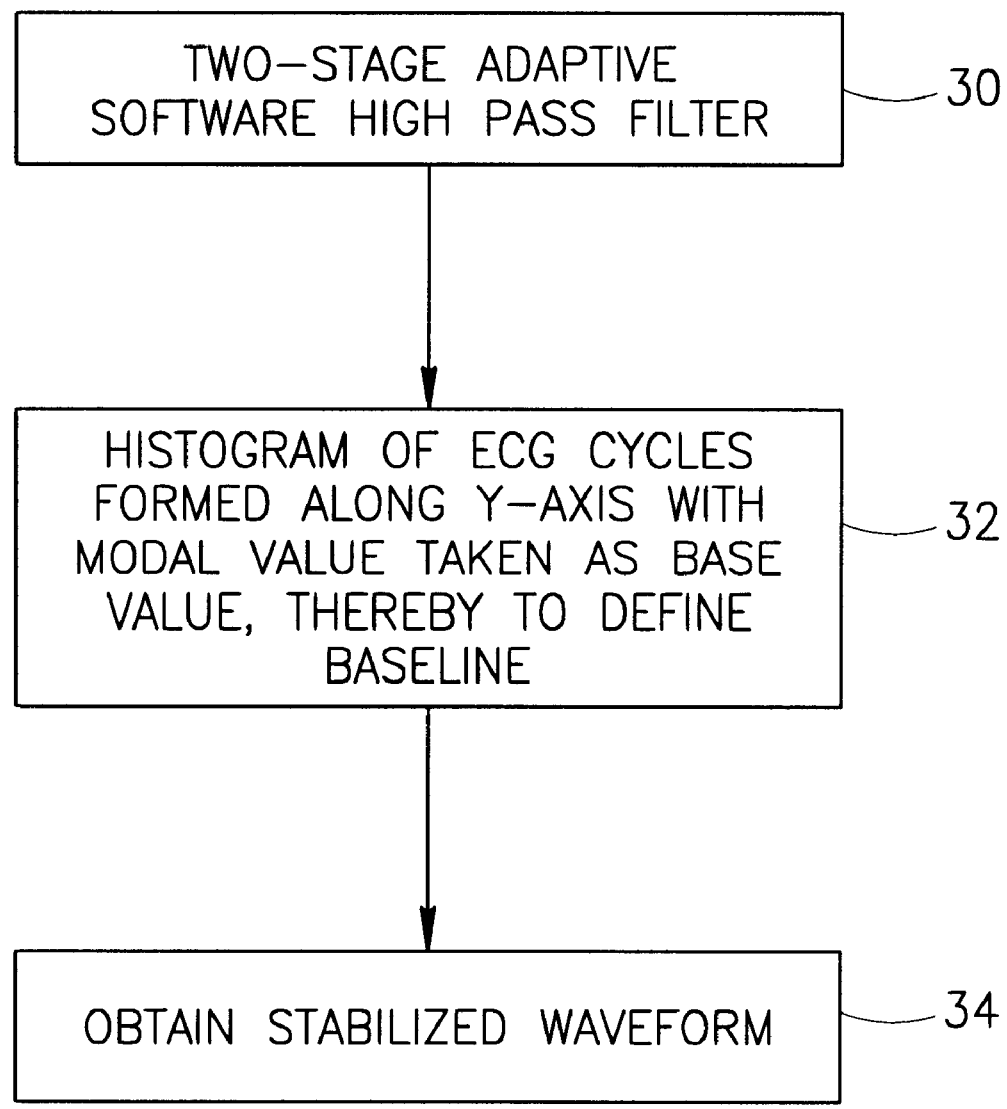
FIG. 3A is a block diagram representation of a novel technique of waveform stabilization employed in the present invention.

Referring now to FIG. 3A, the technique of waveform stabilization of the present invention includes a first stage (block 30) whereat the raw digital data received from the analog-to-digital converter 14 (FIG. 1A) undergoes two-stage adaptive software high pass filtering so as to provide an "adjusted" waveform, and a second stage (block 32) whereat the adjusted waveform is used to determine a baseline for each heart cycle, and a third stage (block 34) whereat the baseline determined for each cycle is used to obtain a stabilized waveform.

Figure 3B:
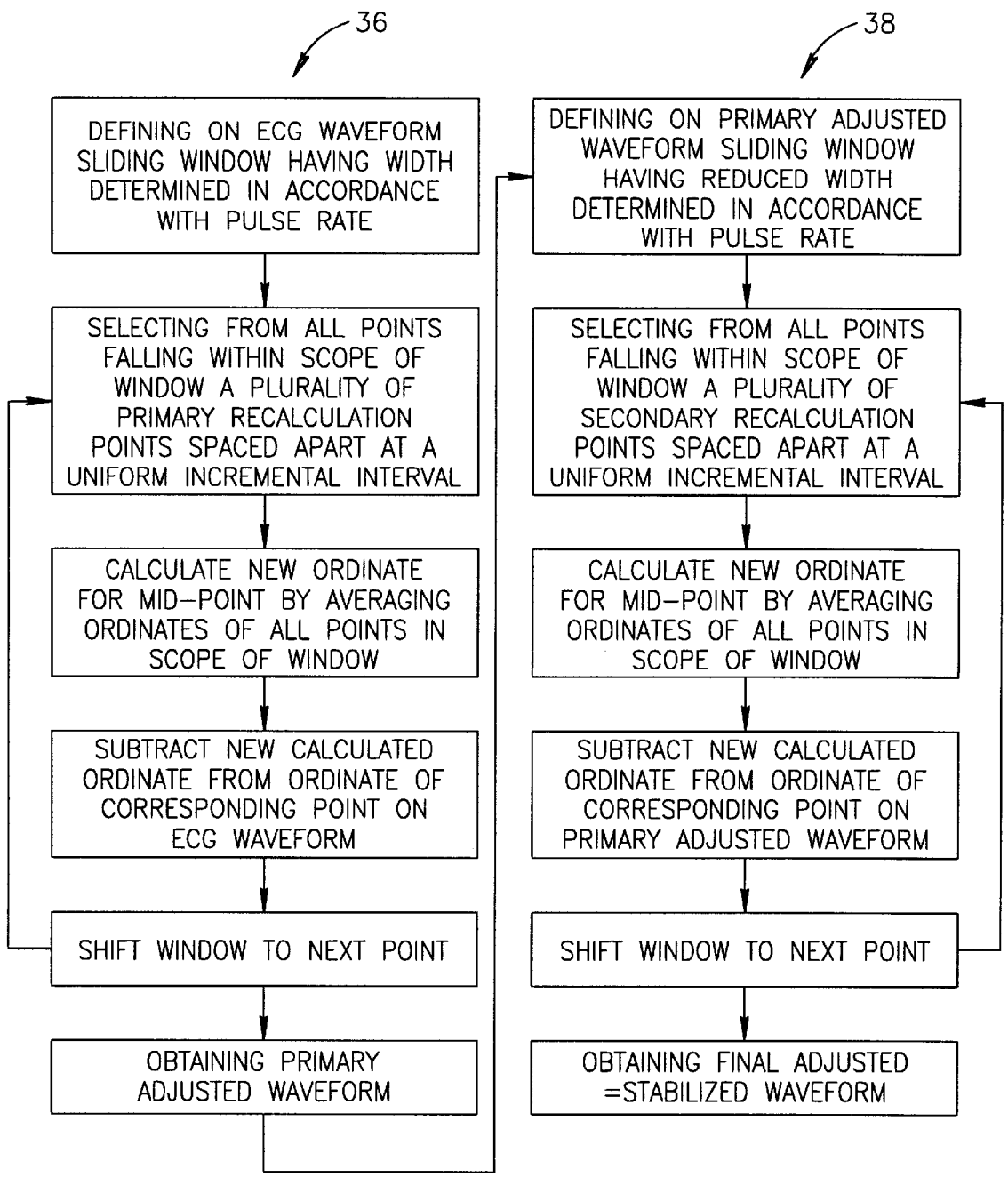
FIG. 3B is a flow chart of the adaptive software filtering employed in the technique of FIG. 3A.
Figure 3C:
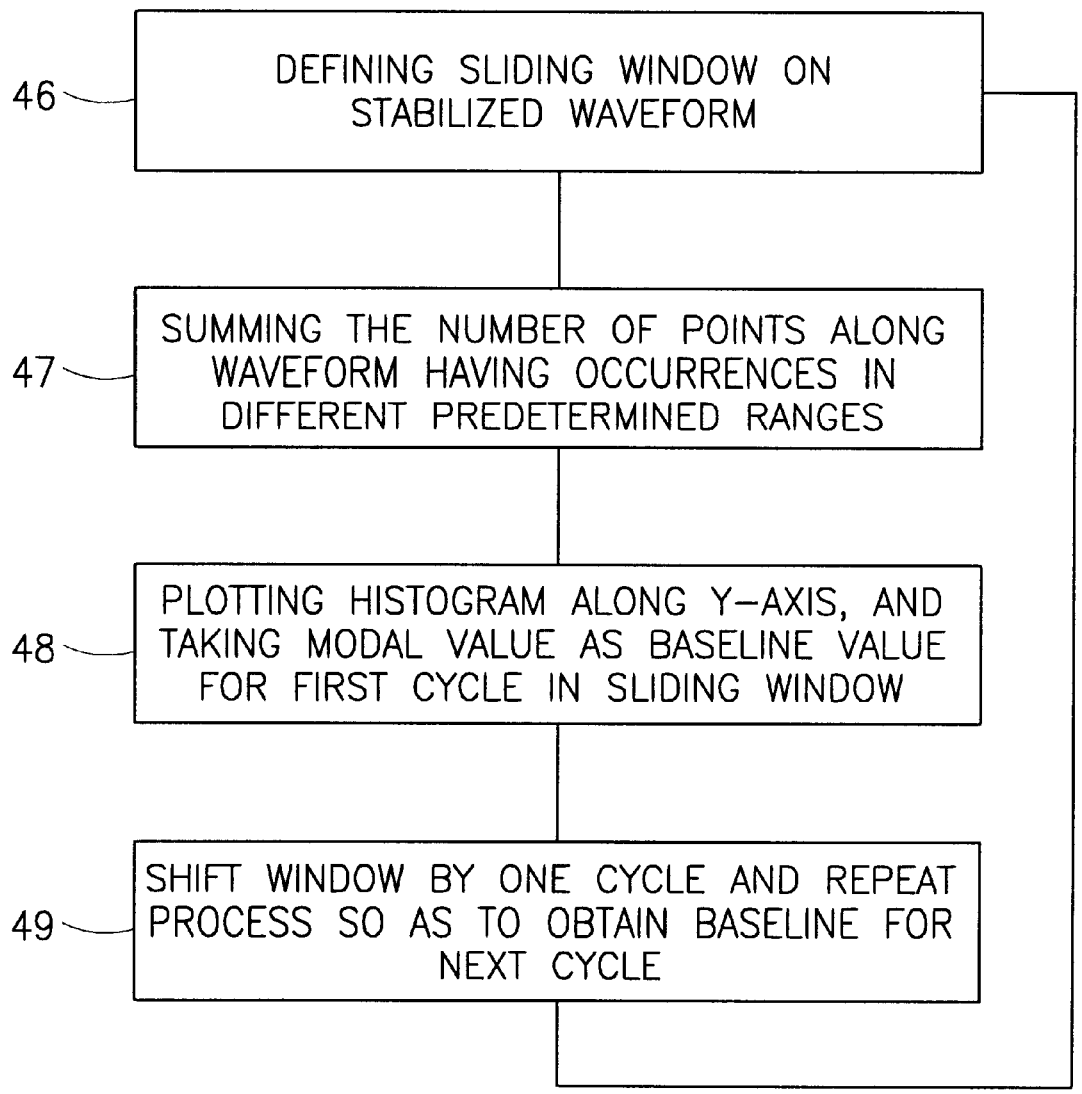
FIG. 3C is a flow chart of histogram formation used for determining the position the baseline in the technique of FIG. 3A.

The stages of filtering and baseline determination are now described in detail in conjunction with FIGS. 3B and 3C, respectively.

As seen in FIG. 3B, preferably two stages of adaptive software high-pass filtering are performed by using a 'sliding window' technique. It has been found by the inventor, that the width of the sliding window may be suitably determined in accordance with the heart rate of the subject. For the first stage, referenced generally 36, a suitable expression defining the sliding window width 'W1,' is $W1 = 2.5 \times R\text{---}R$ where R—R is the time taken by a single heart cycle of the subject.

For the second stage, referenced generally 38, a suitable expression defining the sliding window width 'W2,' is $W2 = W1/1.5$.

Figure 4A:
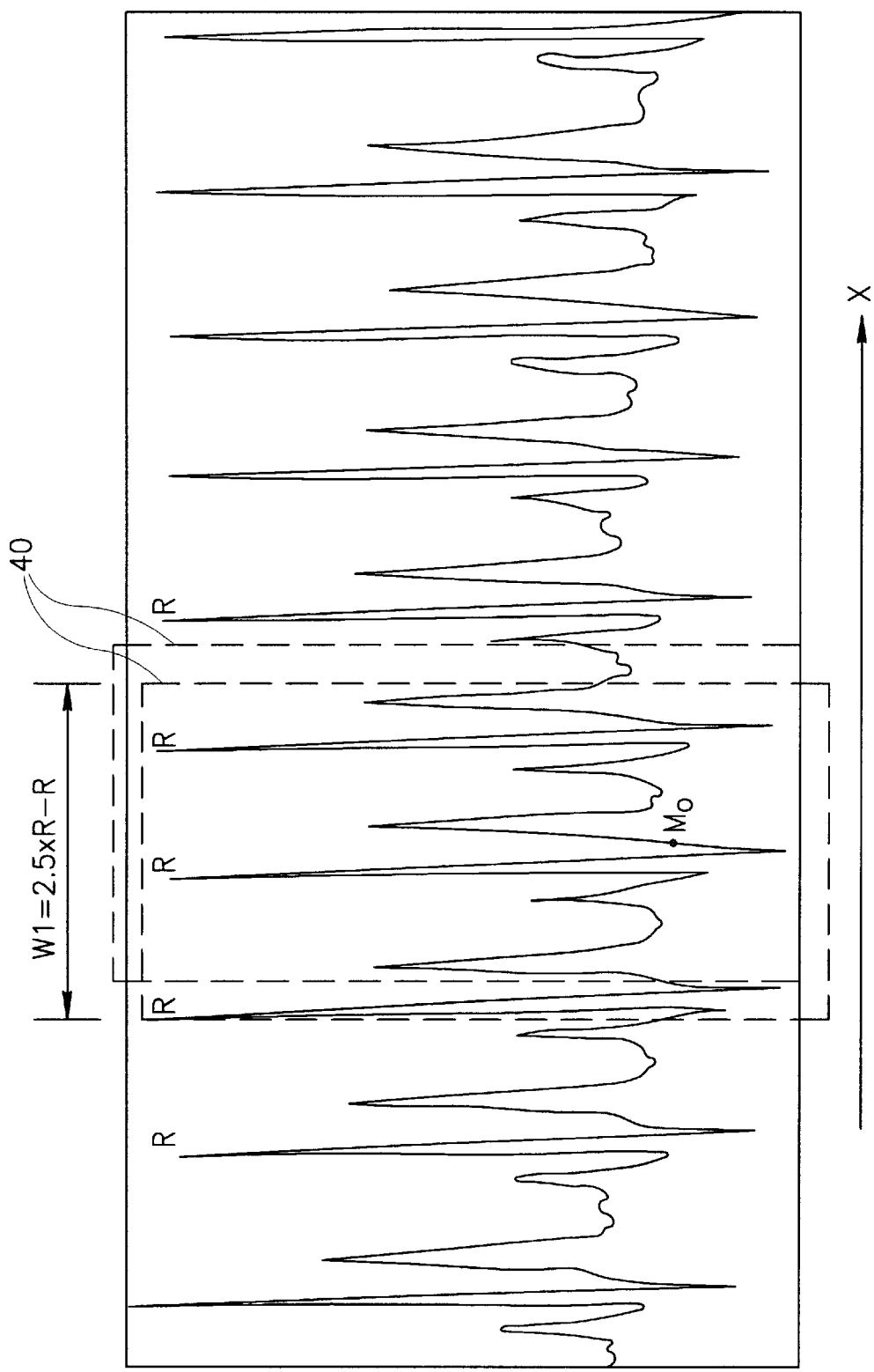
FIG. 4A is a diagram illustrating use of a sliding window technique in the adaptive software filtering technique of FIG. 3B.

In first stage 36, as shown in FIG. 4A, there is defined a window 40, shown in broken lines, whose width is defined in accordance with the expression W1=2.5×R—R. The waveform portion falling within the scope of the window is then divided into a plurality of primary 'recalculation points,' so-called due to the fact that they will be used for recalculating the waveform, and for providing in its place a primary adjusted waveform. The recalculation points are spaced apart by a predetermined uniform incremental interval i. A new ordinate m0' is calculated for mid-point 'M0' of these recalculation points, the new ordinate value being an average of the ordinates of all of the points in the window. The new ordinate is then subtracted form the ordinate of the corresponding point on the original ECG waveform, and the resulting difference is retained as the ordinate of the first point in a new "primary adjusted" waveform, shown at W1. The sliding window is then incrementally shifted along the X axis by a selected increment to 40', and the above process is repeated for each new mid-point M1, M2, ..., Mn, where 'n' is the number of the final primary recalculation point. Once all the points have been recalculated in this manner, a primary adjusted waveform is provided.

The second stage 38 of the filtering technique is similar to the first stage 36, except that, in the second stage, the primary adjusted waveform is subjected to the above-described sliding window recalculation technique, rather than the ECG waveform, and the width of the sliding window is preferably calculated by use of the expression W2=W1/1.5, as brought above. The waveform resulting from second stage 38 is known as the 'final' adjusted waveform.

Figure 4B:
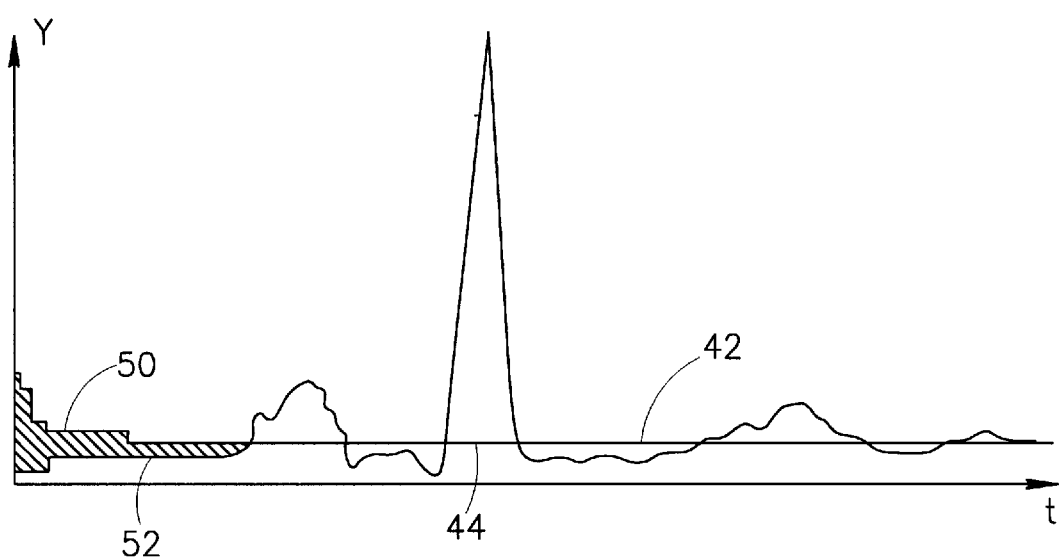
FIG. 4B is an ordinates' histogram superimposed on an ECG waveform as adjusted in accordance with the method of FIGS. 3A–3C.
Figure 5:
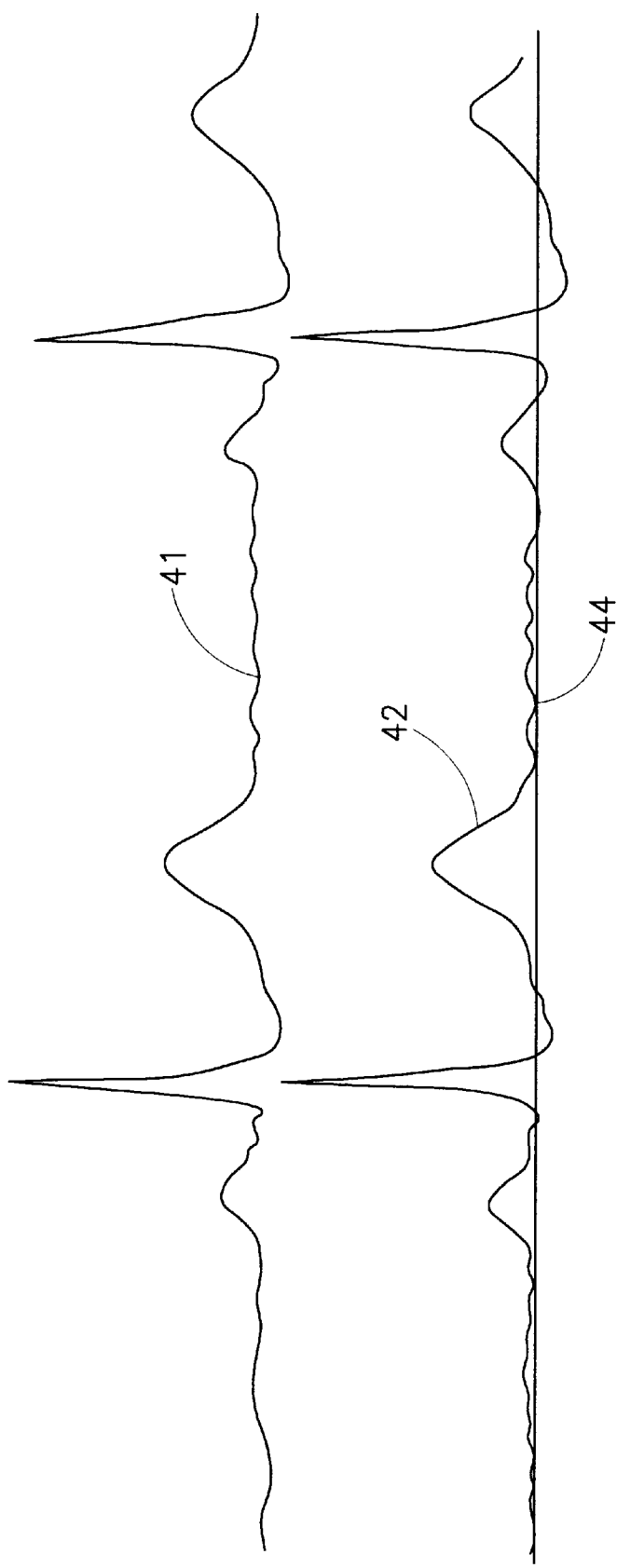
FIG. 5 is a display showing both the original ECG waveform based on raw data, and a waveform adjusted in accordance with a baseline determined as in FIG. 4B.

Referring now to FIGS. 3C and 4B, there is seen the final adjusted waveform 42, together with the baseline 44. FIG. 5 shows an initial waveform 41 based on raw data, and the waveform 42 in stabilized form, together with a baseline 44. The baseline 44 is determined also by use of a sliding window technique, which involves defining a sliding window on the final adjusted waveform (block 46), preferably having a width of two and a half cycles, and summing each number of points along the waveform having ordinate values within a plurality of ordinate ranges (block 47). Once these ordinate value 'occurrences' have been summed, they are plotted as a histogram along the Y-axis, as seen at 50 in FIG. 4B. The mode 52 of the histogram is taken as the baseline 44 for the first cycle in the window (block 48). The window is then shifted by a single cycle, and the same process is performed on the second, third and half of the fourth cycle, so as to obtain a baseline for the second cycle (block 49). In this way each single cycle has determined therefor a separate baseline.

It is noted that there may be discontinuities between baselines for consecutive cycles, indicating significant wander or drift of the original ECG waveform between cycles. In the prior art, such drift may have been redistributed along the entire waveform, thereby leading to misinterpretation of the waveform. It will be appreciated by persons skilled in the art, however, that a separate baseline is calculated for each cycle, and that the baseline determination and subsequent stabilization of the waveform in accordance with the present invention provides for a stabilized waveform that is much more accurate than that provided in the prior art.

Subsequent to the stage of waveform stabilization, it is important to perform a determination of characteristic points. As described above, ECG waveforms are commonly thought of as having six characteristic points, each point being known by a letter in the series PQRSTU and representing a transition or boundary point between two curve portions, wherein each curve portion represents activity of a different intra-heart organ.

Figure 6:
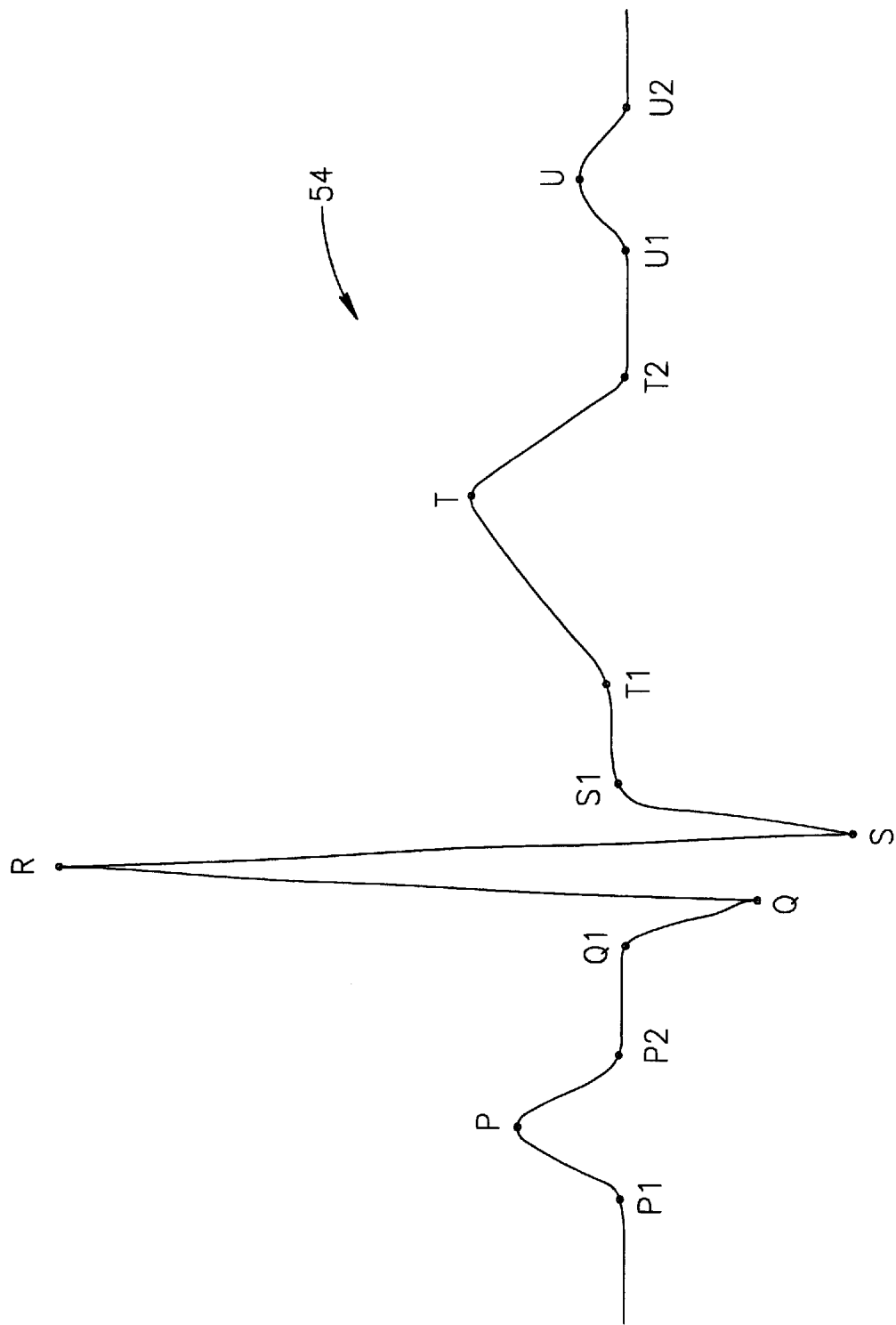
FIG. 6 is an idealized ECG cycle, defining fourteen characteristic points in accordance with a preferred embodiment of the present invention.

Referring now briefly to FIG. 6, there is seen an idealized ECG waveform referenced 54, on which are identified the conventional P, Q, R, S, T, and U points, as well as an additional eight points provided in the present invention, and whose provision is not only facilitated by the very high resolution results obtained by the present invention, but is also necessary so as to identify further exemplary characteristic curve portions found by the inventor to be inherent in all typical ECG waveforms, wherein each portion displays the function of one or more different intra-heart organs. The additional characteristic points are P1, P2, Q1, S1, T1, T2, U1 and U2.

Characteristic points determination is performed in a number of stages, after a copy of the master file has been made, and consists of two stages, as follows:

First Approximation of the Characteristic Points Calculation

First, the R peaks of all the intervals are determined, by identifying the maxima on the stabilized waveform.

Subsequently, the minima points Q and S surrounding the R point, are approximated. These are identified by determining a first derivative of the waveform along the waveform portions immediately preceding and immediately succeeding R. In many cases, particularly of healthy subjects, Q and S are determined as points at which the waveform first derivative changes sign. In some cases, in which Q and S are not identified as clear minima, the points at which the respective values of these first derivatives exceed a predetermined, experimentally obtained threshold values are determined as approximated Q and S points. This first approximation of S is taken as S';

The next stage is determination of the points P1, P2, T1 and T2.

First, the P-wave is approximated by use of the exponential expression $y(x)=Ae^{-\lambda x^2}$ in which y represents the ordinates of the points along the P-wave, A is the maximum of the above exponential expression, which is at the midpoint between P1 and P2, λ is determined from a minimum of the sum of the means square deviations between the ordinates of the waveform and of the above exponential expression.

The distances between P1 and P2 and between T1 and T2 are both determined by the empirically obtained function $k(\lambda,A)x\lambda$. Accordingly, as the position of A is known, it is now possible to determine the respective locations of points P1, P2, T1 and T2.

In order to determine the locations of P and T, third order polynomial approximations of the P- and T-waves are performed, wherein P1 and P2 are two of the roots of the approximation, and the respective third roots are taken as P and T.

Second Approximation

A seventh order polynomial is constructed for the Q-T1 waveform portion. A second approximation of S, taken as S", is determined as the root of this polynomial immediately succeeding R.

As a following step, there is taken a statistically representative number of cycles for both the first and second approximations. The standard deviation σ" of the R-S" intervals is calculated, and these two standard deviations are compared. If σ'<σ", then S occurs at a clear minimum. In this case, S1 is determined as the second root of the above seventh order polynomial succeeding R.

If σ'>σ", then S does not occur at a clear minimum, and in this case, S and S1 coincide at the first root immediately succeeding R.

Q1 exists only in cases in which Q is determined, as above, as a clear minimum. In order to determine Q1, a normal line is extended from Q to the baseline. Q1 is taken to be a point on the baseline located prior to the point at which the normal from Q intersects with the baseline by an interval which is equal to the interval between the intersection point and the point of intersection of the baseline with the QR portion. In other cases, in which Q is not determined as clear minimum, Q and Q1 are taken to coincide.

The same method described above for determining P1, P and P2 is used for determining points U1, U and U2 after averaging, which is described below in conjunction with FIG. 7.

Referring once again briefly to FIG. 1B, once the characteristic points have been determined, the intervals are inherently also known.

Figure 7:
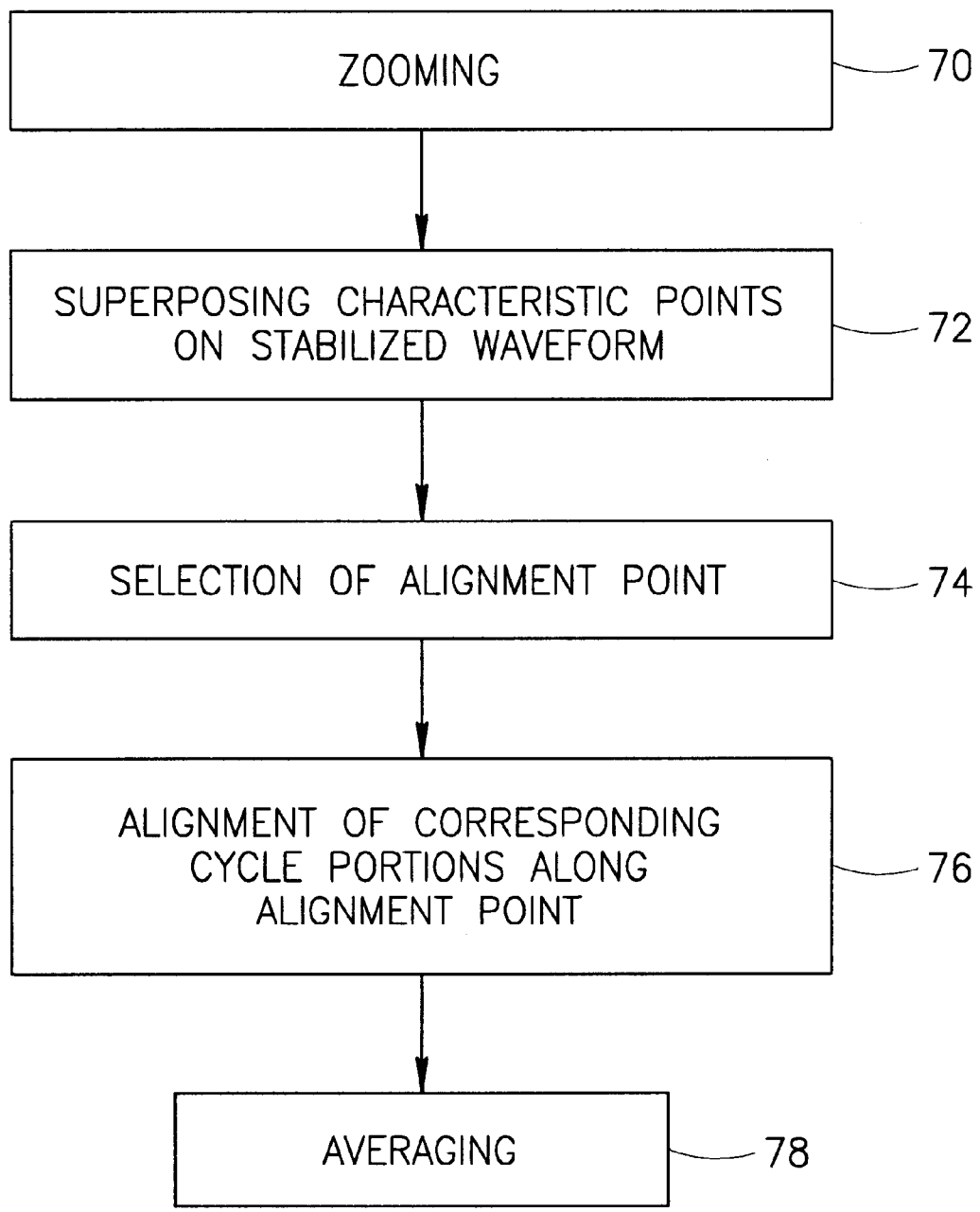
FIG. 7 is a flow chart representation of method steps of waveform processing of the present invention.

Reference is now made to FIG. 7 in which are shown steps of waveform processing performed in accordance with a preferred embodiment of the present invention.

The aim of the waveform analysis described herein is to reveal minute details of the waveform at a resolution significantly greater than that of the prior art waveforms, and so as to substantially improve diagnostic capabilities, and also to facilitate in-depth study of heart activity.

Referring now briefly to FIG. 5, there is seen a stabilized waveform 42, which, as described above, it is subsequently sought to analyze so as to determine at least the fourteen characteristic points shown in FIG. 6, each waveform portion being bounded by a pair of these points representing functions of different intra-heart organs.

It should be noted that, in the description of various method steps that follow, the waveform is stored in digital form as a computer file and may be displayed and manipulated by any suitable conventional computer graphics technique, including selecting specific portions of the waveform, zooming, and the like.

As a first step in analysis of the waveform, indicated at block 70 in FIG. 7, a user—normally a skilled diagnostician—after viewing the entire stabilized waveform (retained as a master file, as described above) on a computer display, may enlarge or zoom into a selected portion of the waveform. It will be appreciated that by zooming into a selected portion of the waveform, there is revealed fine detail not previously visible to the human eye.

Figure 8A:
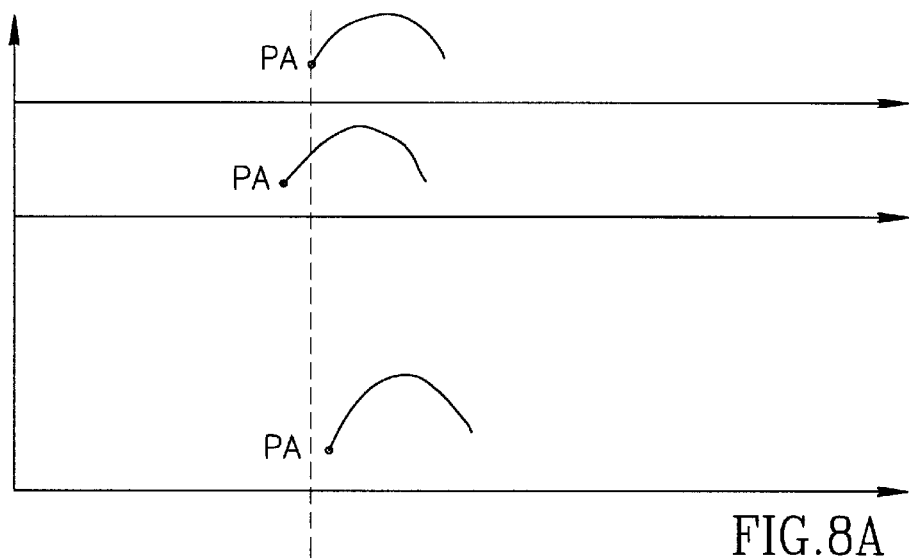
FIG. 8A shows waveform portion samples, taken from different cycles, selected for averaging, prior to alignment, and wherein the starting point of the sample is taken as the alignment point.
Figure 8B:
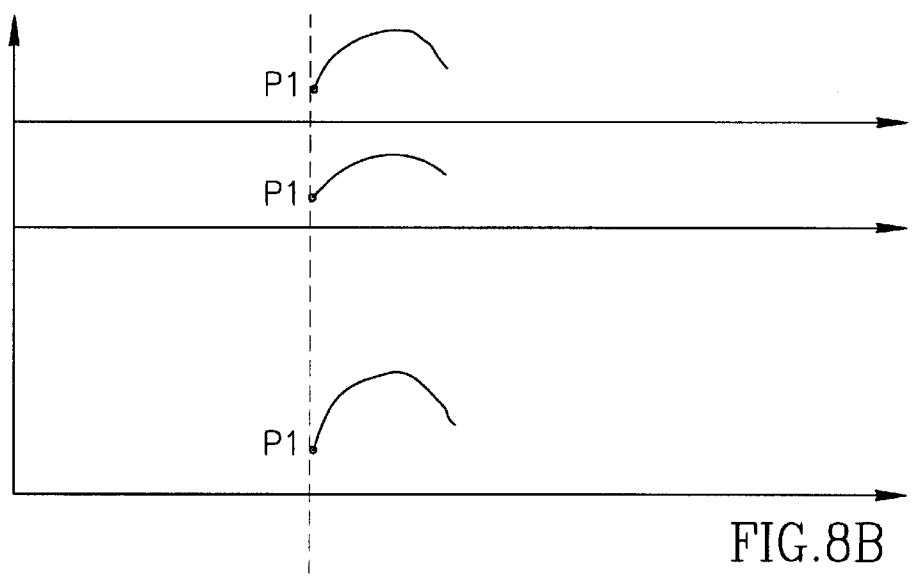
FIG. 8B shows the waveform portion samples after alignment.

Subsequently, after superposing the above-determined characteristic points on the stabilized waveform (block 72), upon identifying an area of the portion which may be of particular interest, the user selects an alignment point (block 74) at the center of this area, as the point which he wishes to see at the highest possible resolution. The alignment point is actually a point "pa" which is found on each of the samples to be aligned, as seen in FIG. 8A. By way of example, if the alignment point is a P1 point (FIG. 6), all the waveform samples are aligned, as seen in FIG. 8B, such that all the P1 points occur at the same time in their respective samples.

Figure 8C:
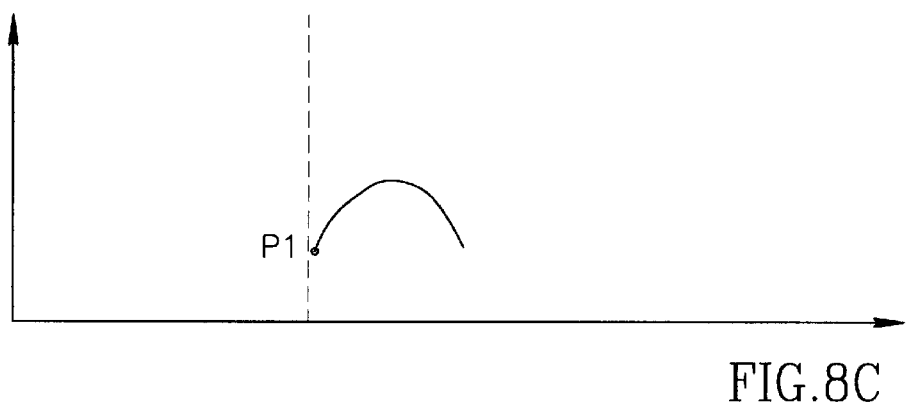
FIG. 8C shows the averaged waveform portion.

As indicated in block 78, after all corresponding samples have been aligned (block 76), they are then averaged, thereby to provide an averaged curve, seen in FIG. 8C, which describes heart activity represented by the portion of the waveform in the immediate vicinity of the alignment point in greatly enhanced clarity. Points along the waveform portion as seen at a resolution which is greatest in the immediate vicinity of the alignment point, and which is lowest at points furthest from the alignment point.

By way of illustrative example, it is known that various features, such as the so-called His bundle, sinus node spike, as well as many others, are contained in the sum of the information provided by the analog signals delivered by electrodes 10 (FIGS. 1A and 1B), but that, in practice, these features are not discernible in prior art ECG, due to the degraded resolution of the waveform provided thereby.

As stated above, an aim of the present invention is to provide a tool by which cardiac electric activity which is detected, as by ECG, may be used for clinical mapping both of the state of a subject's heart at the time of examination, and or trends, thus constituting both a diagnostic and a prognostic tool. A particular advantage of the prognostic aspect of the invention is that, even if no particular problems are indicated in any of the internal heart organs at the time of examination, the same test data providing the diagnostic picture may also be used to indicate a negative trend in terms of one or more internal heart organ functions. Conversely, even if certain problems are indicated in one or more of the internal heart organs at the time of examination, the same test data providing the diagnostic picture may also be used to indicate a positive trend in terms of one or more internal heart organ functions, such as, if the subject is recovering from heart surgery.

The present invention is based on statistical mapping, preferably of ECG data, using a plurality of preselected intercycle and intracycle intervals between preselected characteristic points, determined as described above in conjunction with FIGS. 5, 6 and 7.

Figure 9A:
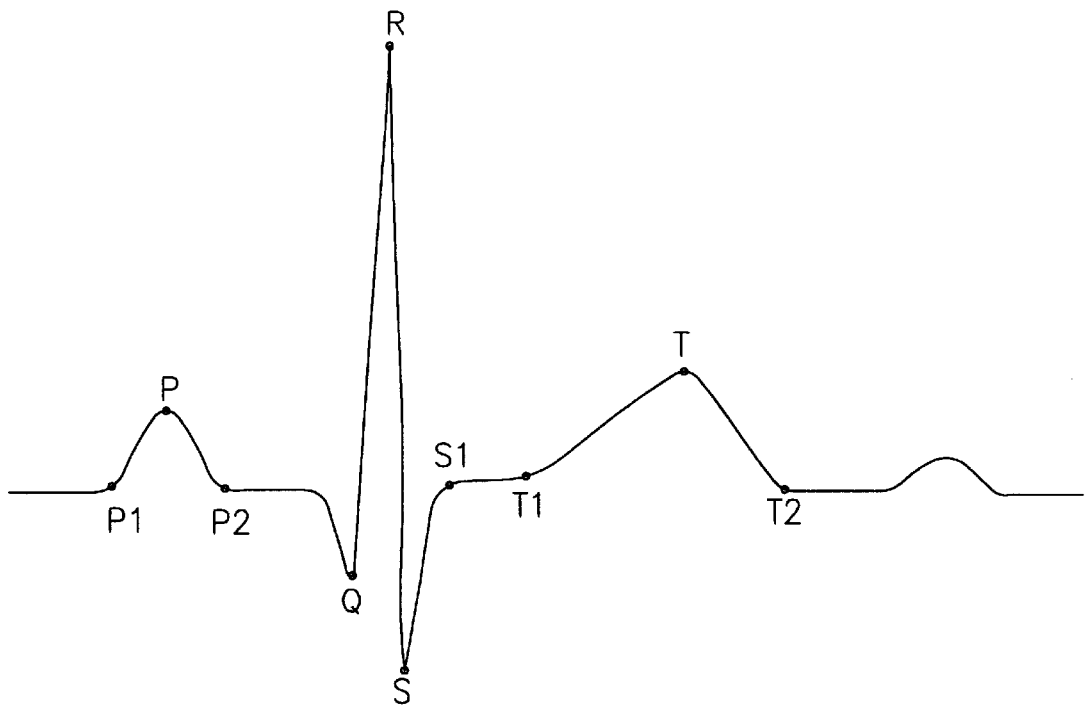
FIG. 9A shows an idealized waveform on which are shown ten characteristic points defining therebetween forty-five intracycle intervals.
Figure 9B:
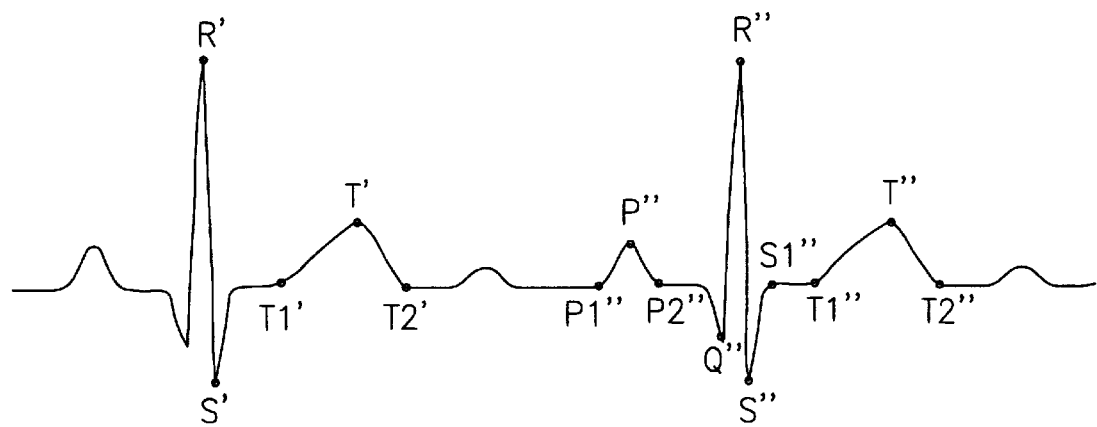
FIG. 9B shows a pair of idealized waveforms on which are shown fifteen characteristic points defining therebetween forty intercycle intervals.

Referring now to FIGS. 9A and 9B, there are shown an idealized waveform for a single heart cycle, and a pair of idealized waveforms for a pair of consecutive heart cycles. Shown on the waveform of FIG. 9A, are ten characteristic points which, among them, define forty-five intracycle intervals, as summarized in Table I, that follows:

TABLE I

ECG Single Crystals Intracycle Intervals Matrix (45 Intervals')

| | P | $P_2$ | Q | R | S | $S_1$ | $T_1$ | T | $T_2$ |
|---|---|---|---|---|---|---|---|---|---|
| $P_1$ | $P_1P$ | $P_1P_2$ | $P_1Q$ | $P_1R$ | $P_1S$ | $P_1S_1$ | $P_1T_1$ | $P_1T$ | $P_1T_2$ |
| P | | $PP_2$ | PQ | PR | PS | $PS_1$ | $PT_1$ | PT | $PT_2$ |
| $P_2$ | | | $P_2Q$ | $P_2R$ | $P_2S$ | $P_2S_1$ | $P_2T_1$ | $P_2T$ | $P_2T_2$ |
| Q | | | | QR | QS | $QS_1$ | $QT_1$ | QT | $QT_2$ |
| R | | | | | RS | $RS_1$ | $RT_1$ | RT | $RT_2$ |
| S | | | | | | $SS_1$ | $ST_1$ | ST | $ST_2$ |
| $S_1$ | | | | | | | $S_1T_1$ | $S_1T$ | $S_1T_2$ |
| $T_1$ | | | | | | | | $T_1T$ | $T_1T_2$ |
| T | | | | | | | | | $TT_2$ |

Furthermore, shown on the dual waveform of FIG. 9B are fifteen characteristic points which, among them, define forty intercycle intervals, as summarized in Table II, that follows:

TABLE II

ECG Dual Cycle Intercycle Intervals Matrix (40 Intervals)

| | $P''_1$ | $P''$ | $P''_2$ | $Q''$ | $R''$ | $S''$ | $S''_1$ | $T''_1$ | $T''$ | $T''_2$ |
|---|---|---|---|---|---|---|---|---|---|---|
| $R'$ | $R'P''_1$ | $R'P''$ | $R'P''_2$ | $R'Q''$ | $R'R''$ | $R'S''$ | | | | |
| $S'$ | $S'P''_1$ | $S'P''$ | $S'P''_2$ | $S'Q''$ | $S'R''$ | $S'S''$ | $S'S''_1$ | | | |
| $T'_1$ | $T'_1P''_1$ | $T'_1P''$ | $T'_1P''_2$ | $T'_1Q''$ | $T'_1R''$ | $T'_1S''$ | $T'_1S''_1$ | $T'_1T''_1$ | | |
| $T'$ | $T'P''_1$ | $T'P''$ | $T'P''_2$ | $T'Q''$ | $T'_1R''$ | $T'_1S''$ | $T'_1S''_1$ | $T'_1T''_1$ | $T'T''$ | |
| $T'_2$ | $T'_2P''_1$ | $T'_2P''$ | $T'_2P''_2$ | $T'_2Q''$ | $T'_2R''$ | $T'_sS''$ | $T'_2S''_1$ | $T'_2T''_1$ | $T'_2T''_1$ | $T'_2T''_1$ |

For each of the above intervals, it is possible to calculate a number of statistical parameters, including M—mean interval length σ—standard deviation of the intervals σ/M×100%—variation coefficient $M_\pi$—mean cycle length $\sigma_\pi$—standard deviation of the cycle length $M/M_\pi$—normalized mean interval $\sigma/\sigma_{90}$ —normalized standard deviation of the intervals.

It will be appreciated that, while M and σ are, of themselves, useful, the corresponding "normalized" M and σ, denoted by $M/M_\pi$ and $\sigma/\sigma_{90}$, are even more useful, in that they represent indices which are equivalent for all tested subjects.

Figure 10:
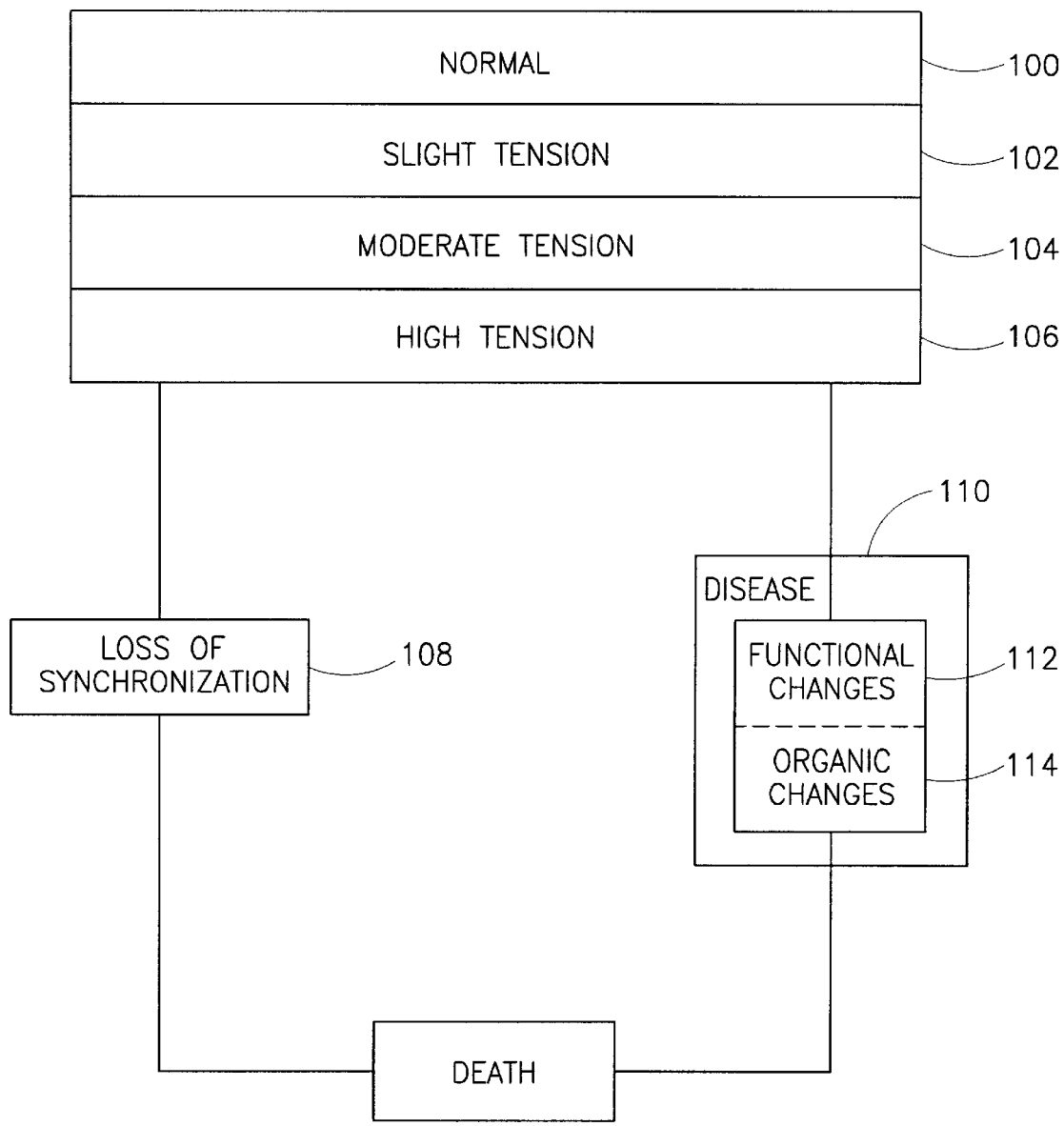
FIG. 10 is a block diagram illustration of a range of physiological conditions of the heart of a subject.

Referring now briefly to FIG. 10, it has been discovered by the inventor that, for healthy subjects, there exists for each different interval "normal" ranges for each statistical parameter. The "normal" condition is indicated in block 100 in FIG. 10. Further ranges also exist, and are shown in FIG. 10 as blocks 102, slight tension; 104, moderate tension; and 106, high tension, all of which indicate cardiac problems which, if not tested, could lead to either loss of synchronization, as seen at block 108, or disease, shown at block 110. Disease itself can be superficially understood as being either a state in which the heart has undergone functional changes, shown at block 112, and which is a reversible state, or, at a more advanced stage of disease, a state in which the heart has undergone organic changes, shown at block 114, and which may be considered irreversible.

The concept described above in conjunction with FIG. 10 may be understood as indicating that, if all the parameters evaluated for a given interval and for a particular subject, fall within the normal ranges for that interval, then the activity of the intra-heart organ or organs with which that interval is associated is also normal. On the other hand, should any of these parameters fall outside the normal range, this is an indication of a certain degree of abnormality of the activity of the intra-heart organ or organs with which that interval is associated, thus revealing the degree of severity thereof.

It should, of course, be understood that the progression of conditions shown in FIG. 10 is not intended to convey a one-way progression of a healthy person through increasingly severe conditions. Rather, it should be understood that the illustrated progression is indicative of a number of conditions which, if indicated by diagnostical or prognostic evaluation of ECG data, as in the present invention, are, on the whole, reversible.

Tests were performed by the inventor on 100 healthy subjects, in order to establish the above-mentioned normal ranges for all intervals and for all parameters. 80% of the examined subjects were female, and were classified in two age ranges, namely, 30–40 and 40–50 years of age. The bulk of these tests were carried out on 87 subjects between Oct. 20–24$^{th}$, 1996.

During the tests, a number of persons known to have cardiac conditions were examined. These included a 65 year old female with an SN-node bradycardia, whose condition was clearly indicated by test results, as described below in conjunction with FIGS. 15A–16B and Table IV.

As known, each interval reflects the cardiac activities of certain internal heart organs or groups thereof, and understanding of statistical behavior of these intervals casts light on the condition of the heart organ or organs to which the interval relates.

It has furthermore been found that the heart condition of any subject may be expressed graphically as a set of "dynamic fingerprints," which provide a clear and explicit visual indication of the existence of any abnormalities in any internal heart organ or group of internal heart organs.

Figure 11:
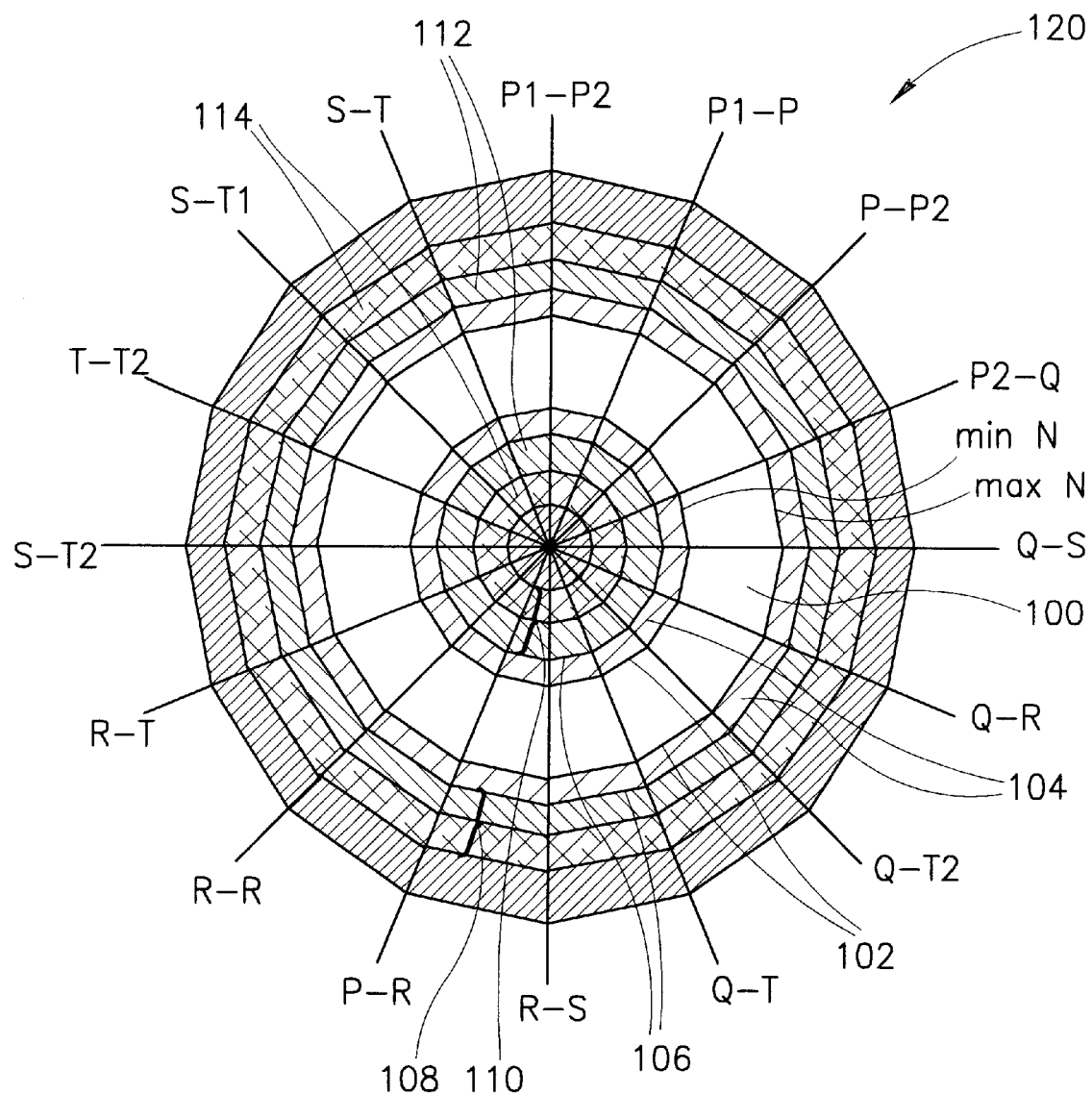
FIG. 11 shows a multi-axis reference system for multiple interval fingerprint plots indicating the physiological state of the heart of a subject.

Referring now to FIG. 11, each fingerprint is based on a multiple interval plot on a multi-axis reference system, shown generally at 120. The reference system consists of a plurality of axes radiating from an origin, wherein each axis defines a scale on which is indicated a range of possible values of a predetermined one of the above statistical parameters, obtained for a predetermined interval.

The reference system 120 of FIG. 11 is, in effect, a direct parallel to the series of conditions described above in conjunction with FIG. 10.

As will be further appreciated from the description of plots shown and described below in conjunction with FIGS. 12A and 12B, the fingerprint consists of a closed-form plot through points indicated on the axes in accordance with the value of the particular parameter obtained for each interval. It will be appreciated, therefore, that each plot thus shows the values of a single parameter for all selected intervals for a given subject at the time of testing, thereby constituting one of a set of dynamic fingerprints representative of his heart condition.

The reference system of FIG. 11 shows a plurality of axes, on each of which may be indicated the value of a statistical parameter for a predetermined interval. Although only sixteen intervals are indicated in the illustrated reference system, the same sixteen intervals being indicated in the plots of FIGS. 12A and 12B, this is by way of example only, and, in practice, the reference system may consist of any suitable number of intervals, but preferably no more than the forty-five intracycle intervals and forty intercycle intervals described above in conjunction with FIGS. 9A and 9B.

It is seen that all the interval axes extend through a series of concentric circular or ring-like regions each of which corresponds to one of the clinical stages shown in FIG. 10, and, in conjunction with the individual intervals, this serves to indicate which interval heart organs may be the cause of the expected cause of a particular clinical situation. Accordingly, the reference numerals in FIG. 10 are used to indicate corresponding regions in the reference system of FIG. 11. It is thus seen that, in reference system 120, the broadest region is the normal region 100, which is bounded by upper and lower boundaries "max N" and "min N", each of which represent statistically determined upper and lower values for a plotted parameter. Movement beyond the boundary values max N and min N is inherently movement into an intermediate range, denoted, for conveniences, by reference numeral 104. The boundaries 102 and 106 of intermediate range 104, respectively demarcate a transition between normal, slight tension and moderate tension, and a transition between moderate tension, high tension, and moderate tension, and a transition between moderate tension, high tension, and disease or loss of synchronization.

A first region of disease 112 indicates functional changes, and a second region 114, bordering on the first region 112, indicates more serious disease, in which organic changes have occurred in the heart. These two regions taken together, are indicated both by reference numerals 108, indicating loss of synchronization, and by 110. While loss of synchronization is not necessarily disease, it nonetheless indicates a serious deterioration in cardiac performance. The regions shown in black are for graphic illustration only, and serve to indicate that a value occurring beyond regions 112 and 114 indicate a terminal condition. It should also be noted that, from any particular plot it is possible to see not only whether the subject has a problematic condition, but also, depending along which interval axis this condition is observed, the internal heart organ where the problem lies.

Figure 12A:
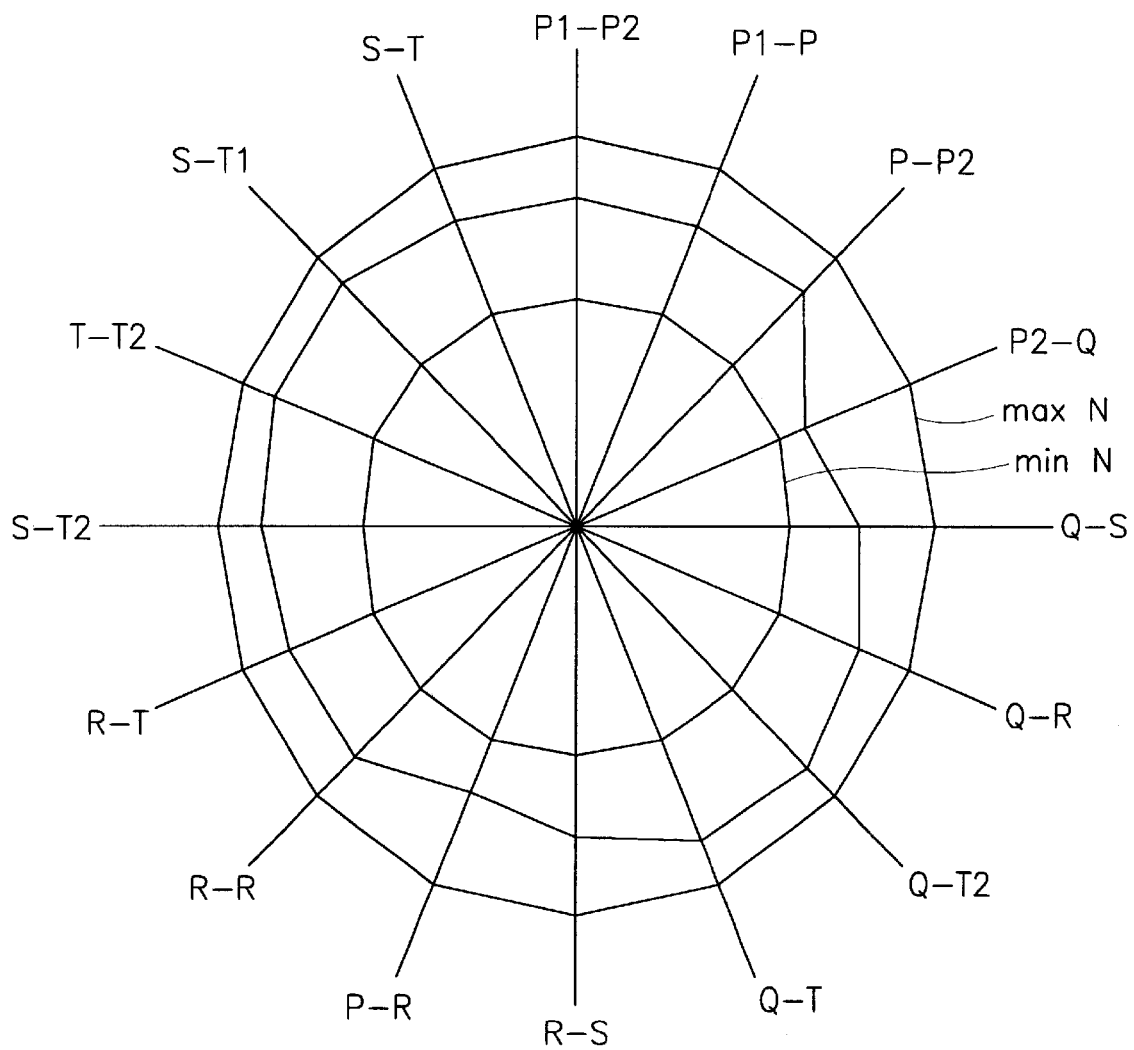
FIGS. 12A and 12B are fingerprint plots based on ECG test data, for mean cycle lengths and standard deviation, respectively.
Figure 12B:
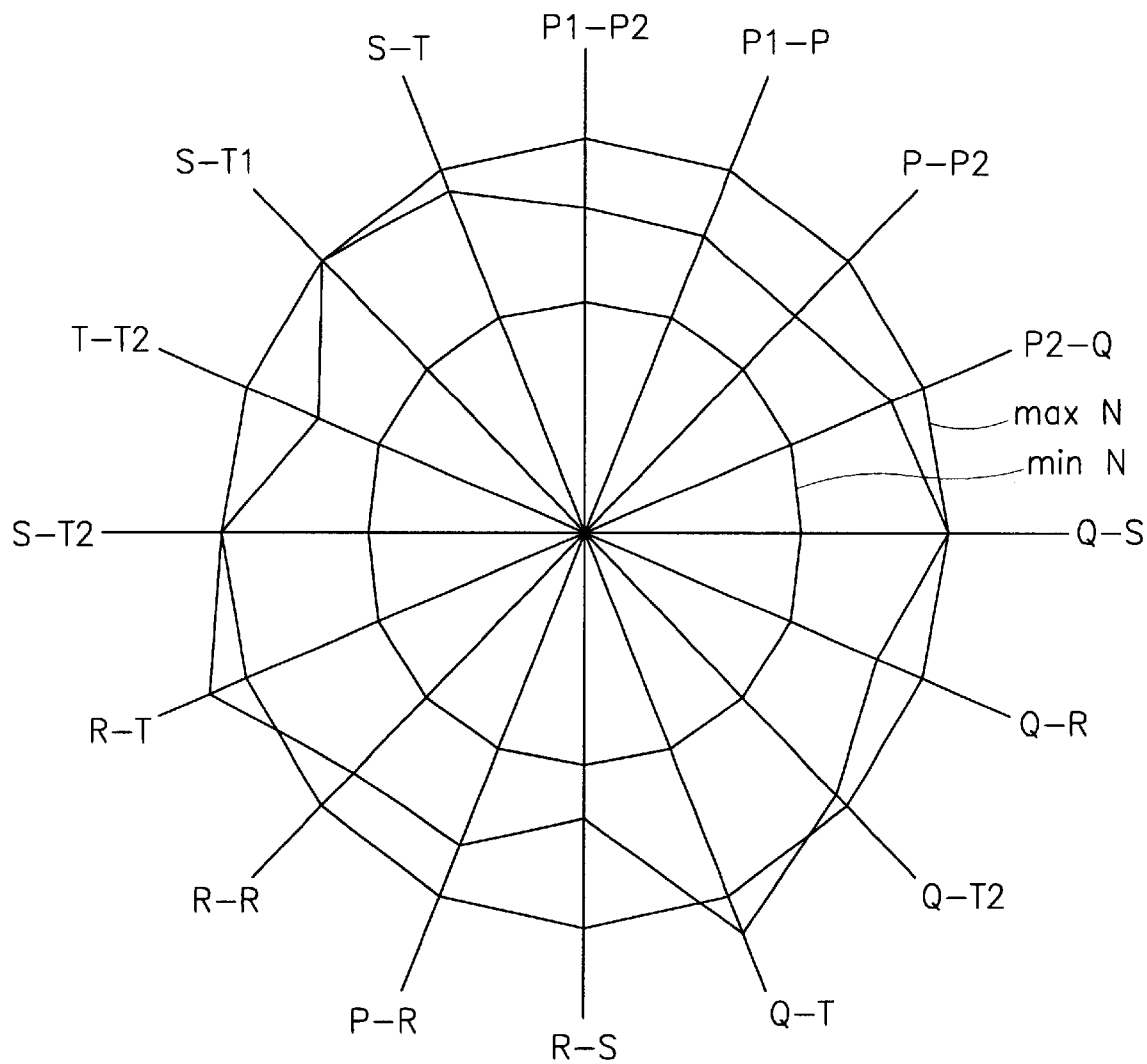

Referring now to FIGS. 12A and 12B, there are shown two plots of different parameters for a tested subject. The only region of the multi-axial reference system 120 of FIG. 11 that is indicated in the present drawings is the normal region 100. The plot of FIG. 12A is for the M parameter, and is seen to be entirely within the normal range. The plot of FIG. 12B, however, is for the σ parameter, and is seen to be close to the upper boundary "max N" and, for values of σ evaluated for the S-T2, R-T, Q-T, Q-T2 and Q-S intervals, is seen to coincide with or cross upper boundary "max N."

It will be appreciated that the difference between the apparently normal plot for M and the abnormal plot for σ is due not to an actual discrepancy between these two sets of evaluated statistical parameters, but to a difference in what the two parameters indicate.

Whereas the M parameter indicates the condition of the subject at the time of testing, showing that there are no existing problems, the σ parameter indicates that the apparently normal subject is showing the first signs of problematic conditions in the performance of the internal heart organs described, in the present example, at the S-T2, R-T, Q-T, Q-T2 and Q-S intervals.

The data on which the plots of FIGS. 12A and 12B are based, are shown in the following table. It will be appreciated that, FIG. 12A, the normal range is as per column (2) of the table, and the plotted test data, providing the illustrated fingerprint, is as shown in column (3). Similarly, in FIG. 12B, the normal range is shown in column (4), and the plotted test data, providing the illustrated fingerprint, is as shown in column (5). Columns (6) and (7) show normal range values and test data obtained from the same subject whose fingerprints are shown in FIGS. 12A and 12B, for "normalized M," shown as $MM_m$ while columns (8) and (9) show normal range values and test data obtained, also from that same subject, for "normalized standard deviation σ," shown as $\sigma/\sigma_{rr}$.

TABLE III

Normal & Test Values for Statistical Parameters M, σ, $M/M_\pi$ and $\sigma/\sigma_\pi$ for 16 Intracycle Intervals

| (1) Interval | (2) M (Normal Range) | (3) M (Test Data) | (4) σ (Normal Range) | (5) σ (Test Data) | (6) $M/M_\pi$ (Normal Range) | (7) $M/M_\pi$ (Test Data) | (8) $\sigma/\sigma_\pi$ (Normal Range) | (9) $\sigma/\sigma_\pi$ (Test Data) |
|---|---|---|---|---|---|---|---|---|
| P1-P2 | 120.9 ± 30.6 | 129.6 | 8.4 ± 4.7 | 8.1 | 0.14 ± 0.03 | 0.15 | 0.224 ± 0.101 | 0.169 |
| P1-P | 61.3 ± 16.0 | 64.8 | 4.1 ± 2.5 | 4.0 | 0.07 ± 0.02 | 0.07 | 0.110 ± 0.053 | 0.084 |
| P-P2 | 59.6 ± 14.7 | 64.8 | 4.5 ± 2.3 | 4.0 | 0.07 ± 0.01 | 0.07 | 0.120 ± 0.049 | 0.084 |
| P2-Q | 51.2 ± 26.4 | 34.5 | 5.3 ± 2.5 | 6.3 | 0.06 ± 0.02 | 0.04 | 0.143 ± 0.043 | 0.132 |
| Q-S | 70.8 ± 26.2 | 69.5 | 2.7 ± 1.1 | 4.5 | 0.08 ± 0.03 | 0.08 | 0.072 ± 0.024 | 0.094 |
| Q-R | 30.3 ± 4.7 | 31.5 | 2.7 ± 2.2 | 3.4 | 0.04 ± 0.00 | 0.04 | 0.073 ± 0.046 | 0.072 |
| Q-T2 | 374.1 ± 45.0 | 394.4 | 4.4 ± 1.5 | 5.8 | 0.45 ± 0.04 | 0.45 | 0.118 ± 0.032 | 0.122 |
| Q-T | 291.7 ± 34.8 | 303.3 | 2.7 ± 1.0 | 4.0 | 0.35 ± 0.03 | 0.34 | 0.071 ± 0.022 | 0.084 |
| R-S | 40.4 ± 25.3 | 38.0 | 2.4 ± 1.5 | 1.7 | 0.05 ± 0.02 | 0.04 | 0.065 ± 0.031 | 0.037 |
| P-R | 141.1 ± 32.3 | 130.7 | 2.2 ± 1.2 | 2.7 | 0.17 ± 0.03 | 0.16 | 0.059 ± 0.026 | 0.056 |
| R-R | 837.0 ± 172.4 | 884.2 | 37.4 ± 24.2 | 47.7 | 1.00 ± 0.00 | 1.00 | 1.000 ± 0.000 | 1.000 |
| R-T | 261.4 ± 35.1 | 271.8 | 1.8 ± 0.3 | 2.4 | 0.31 ± 0.03 | 0.31 | 0.047 ± 0.006 | 0.050 |
| S-T2 | 303.4 ± 47.7 | 325.0 | 4.0 ± 1.6 | 6.0 | 0.36 ± 0.05 | 0.37 | 0.106 ± 0.033 | 0.126 |
| T1-T2 | 167.6 ± 26.6 | 182.3 | 10.1 ± 4.9 | 8.9 | 0.20 ± 0.03 | 0.21 | 0.270 ± 0.105 | 0.186 |
| S-T1 | 121.6 ± 33.9 | 142.8 | 2.9 ± 1.3 | 3.9 | 0.15 ± 0.03 | 0.16 | 0.078 ± 0.027 | 0.082 |
| S-T | 221.0 ± 38.5 | 233.9 | 2.9 ± 0.8 | 2.4 | 0.26 ± 0.04 | 0.26 | 0.054 ± 0.017 | 0.051 |

A particular advantage of the "dynamic fingerprinting" described above is that it allows the condition of a subject to be assessed at a glance. Furthermore, evaluation and display of the above-mentioned statistical parameters in accordance with the present invention, despite their inherent value, are not revealed by known methods, and constitute a valuable tool for assessing cardiac activity, whether taken alone or in conjunction with ECG or other methods of analysis.

As further evidence of the utility of the present method of statistical variability measurement and display, and referring to FIGS. 15A–16B, as well as to Table IV below, there are provided experimental data and fingerprint plots for a 65 year old female with an SN-node bradycardia, derived from an ECG test performed in late October 1996.

Figure 15A:
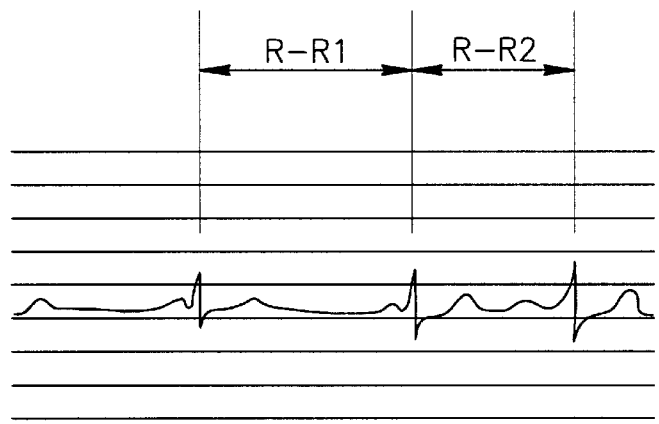
FIGS. 15A and 15B are waveforms of a subject tested in accordance with the method of the present invention.
Figure 15B:
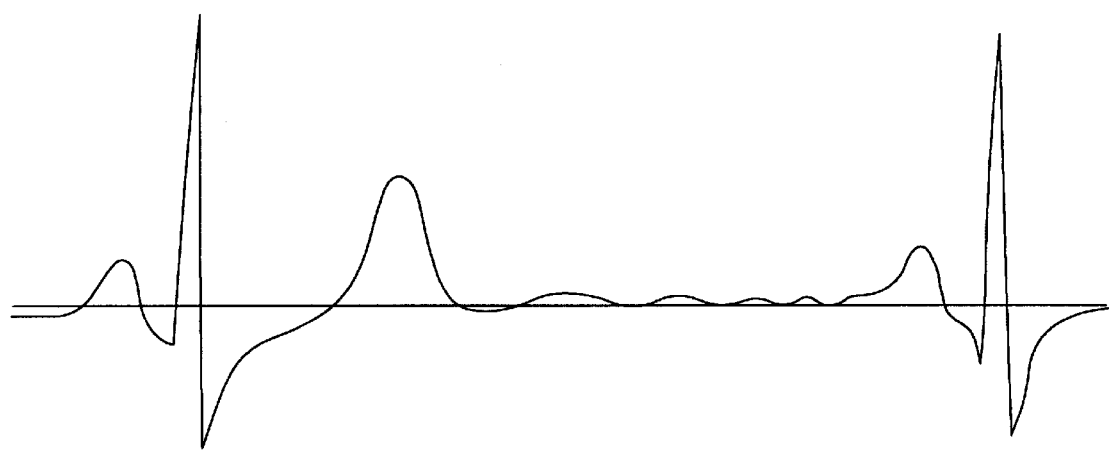
Figure 16A:
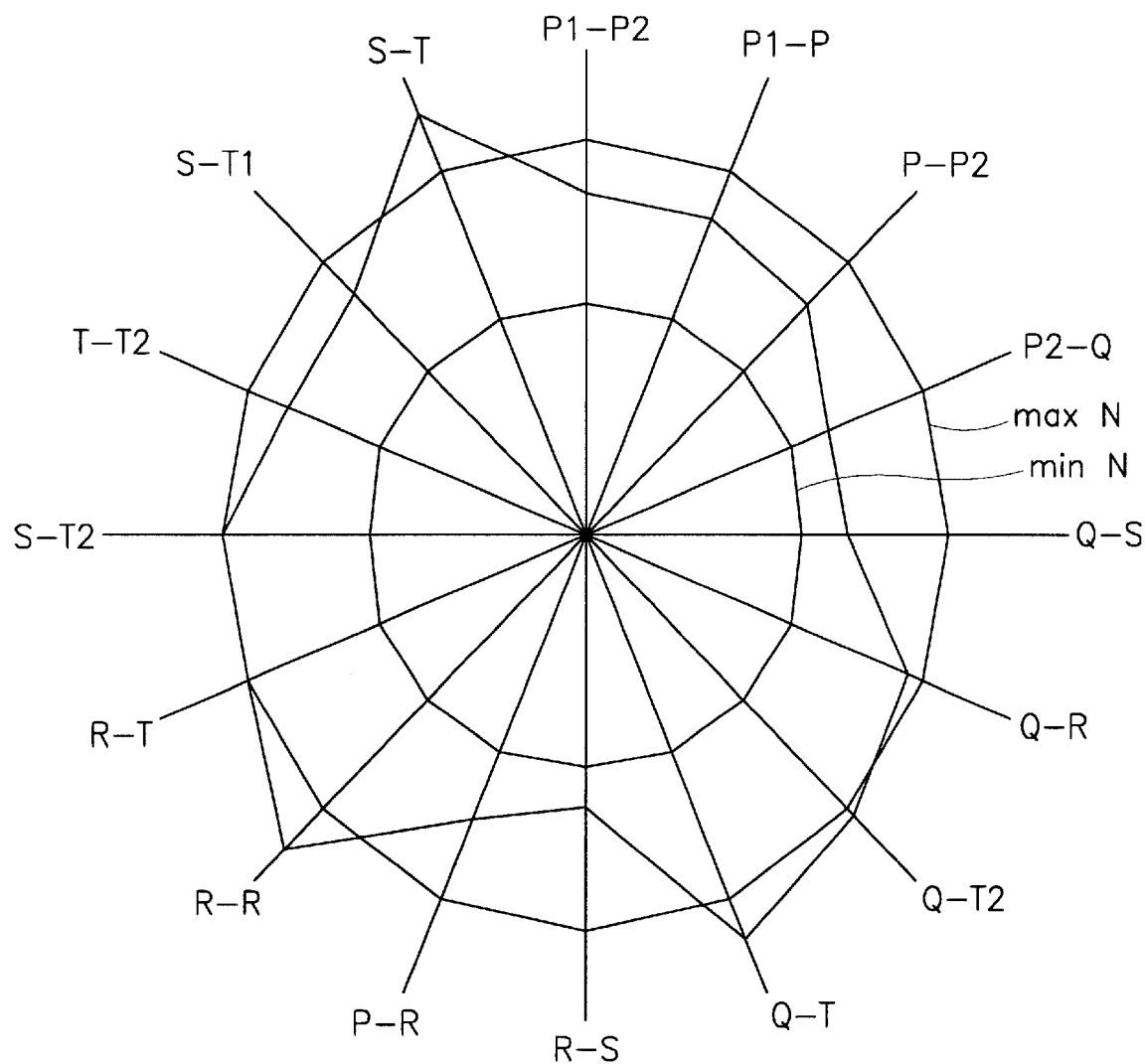
FIGS. 16A and 16B are fingerprint plots of statistical data obtained from the ECG waveforms of FIGS. 15A and 15B, for mean cycle lengths and standard deviation, respectively.
Figure 16B:
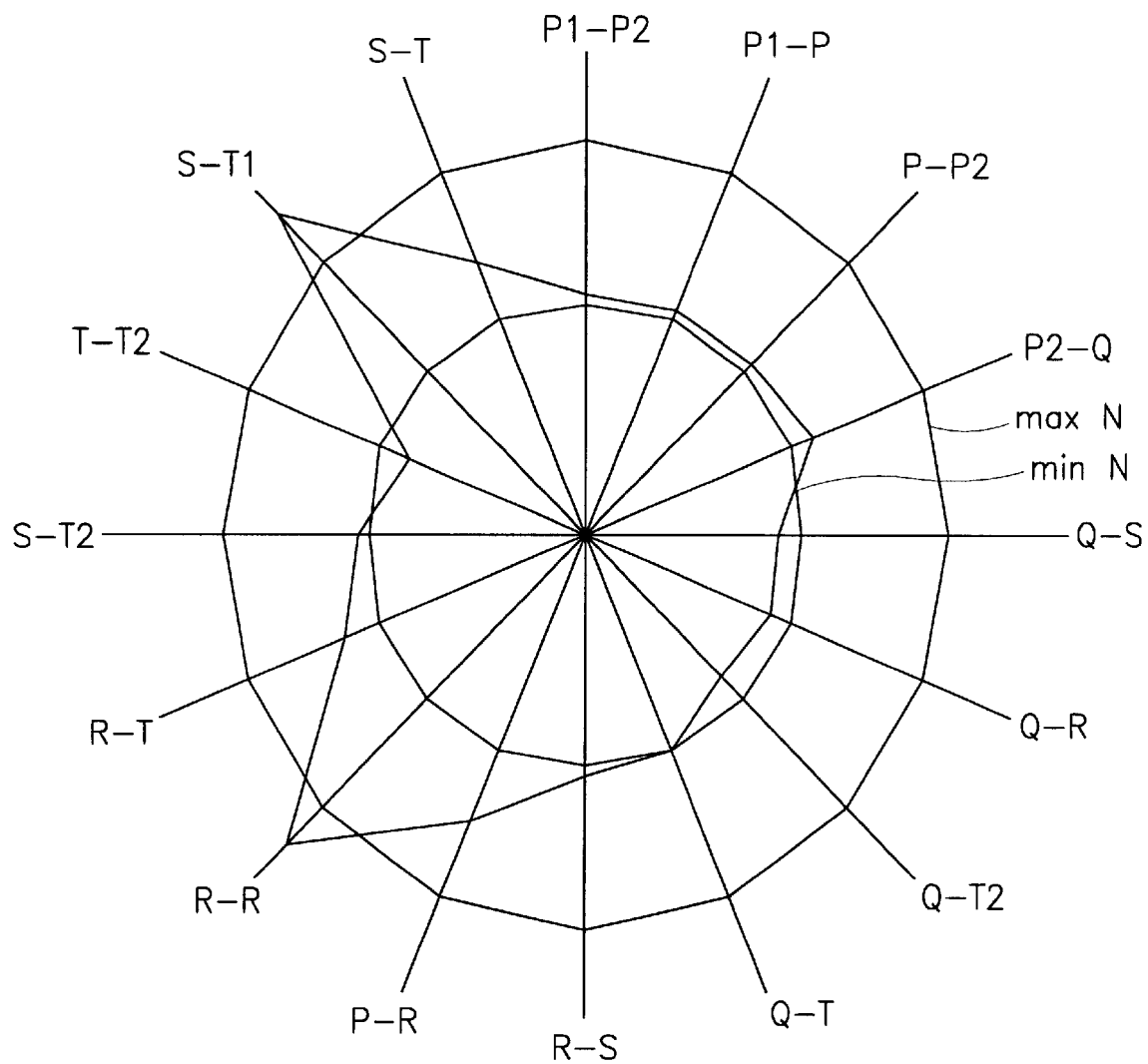

FIG. 15A is an ECG plot performed by a prior art method, while FIG. 15B shows a stabilized waveform performed by a method of the invention, with a sampling rate of 750 times per second. Neither the waveform sample seen in FIG. 15A, nor the stabilized waveform of FIG. 15B, discloses any immediately apparent heart problems of the subject, apart from an unstable heart beat, reflected in the clear difference between the R—R intervals, shown as R–R$_1$ and R–R$_2$ in FIG. 15A.

Notwithstanding the apparent normality of the subjects's heart condition, statistical analysis of the stabilized waveform seen in FIG. 15B, in accordance with the present invention, provided results which clearly reflect her disease.

In more detail, the quantities M, $\sigma$, M/M$_{rr}$ and $\sigma/\sigma_{rr}$ for 16 intracycle intervals were calculated, and are listed alongside the values of the normal range in Table IV below. Subsequently, as for the data of Table III, shown as the fingerprint plots in FIGS. 12A and 12B above, the M and $\sigma$ data of the present subject was plotted, in a similar manner, on the reference system 120 (FIG. 11) of the present invention. As is immediately evident from the closed form plots of FIGS. 16A and 16B, there are clear abnormalities in the present subject's test data.

healthy at the time of testing. As seen, the two plots shown a higher degree of correlation, clearly demonstrated by the overlap of the two shaded areas, 1 and 2, in the drawing.

Figure 13:
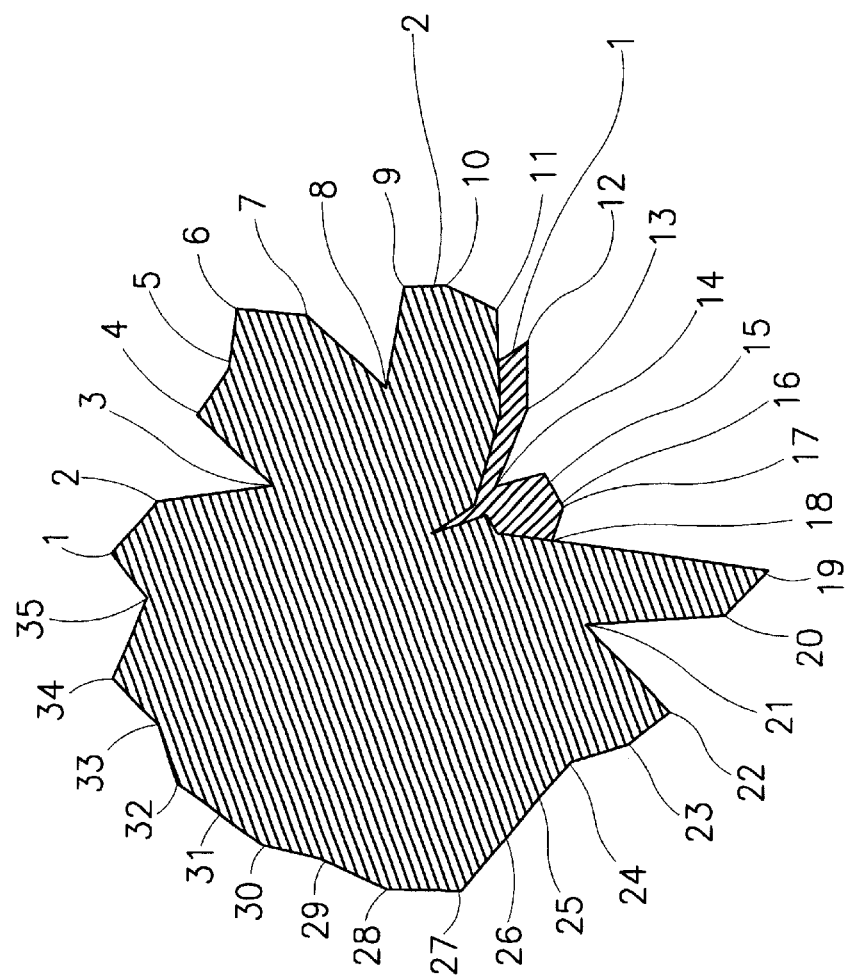
FIGS. 13 and 14 are a pair of comparative superimposed plots for a pair of healthy subjects, showing a high degree of correlation, and for a pair of subjects of which one is healthy and the other is known to have a heart condition, respectively.
Figure 14:
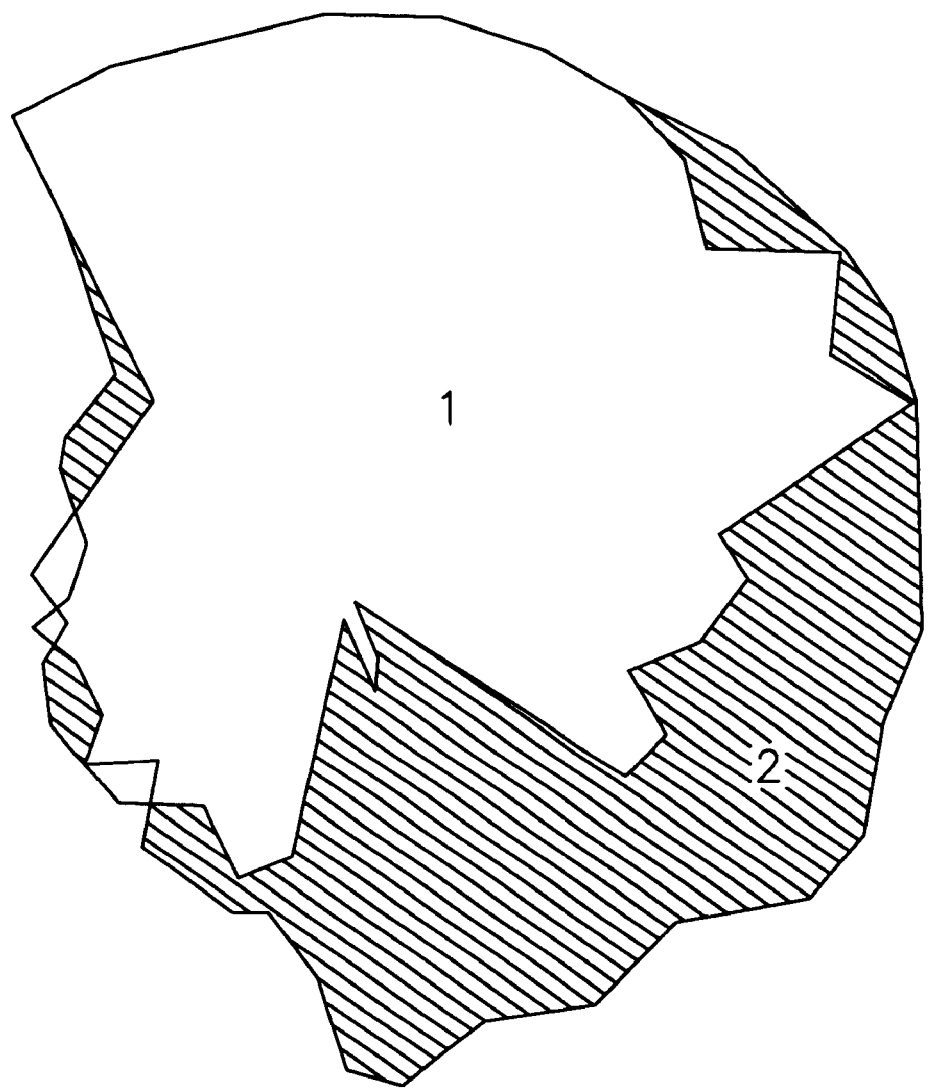

In contrast to the results illustrated in FIG. 13, in FIG. 14 there are shown, in a similar manner, a further two sets of M for intracycle intervals originating at Q, for a different pair of subjects. In this case, while one of the subjects was known to be healthy, the other was known to have undergone bypass surgery. The contrast between their conditions is clearly demonstrated by the shaded areas 1 and 2, which are seen to overlay only partially, there having been evaluated a statistical correlation between them of only 53%.

It will be appreciated by persons skilled in the art that, while the data shown in FIGS. 13 and 14 were obtained by evaluating thirty-five intracycle intervals in the case of FIG. 13, and forty such intervals in the case of FIG. 14, this difference is not significant, and it thus remains possible to compare the data, as above.

It will be appreciated by persons skilled in the art that the scope of the present invention is not limited by what has been specifically shown and described hereinabove, merely by way of example. Rather, the scope of the invention is limited solely by the claims, which follow.

What is claimed is:

1. A methods of providing an indication of the physiological state of the heart of a mammal by the following steps:

detecting periodic activity of internal heart organs in a sequence of heart cycles;

observing a predetermined physical quantity characteristic of a selected activity;

evaluating predetermined statistical parameters of the predetermined physical quantity for a selected number of the sequence of heart cycles; and

TABLE IV

Normal & Test Values for Statistical Parameters M, $\sigma$, M/M$_\pi$ and $\sigma/\sigma_\pi$ for 16 Intracycle Intervals for Case Study

| (1) Interval | (2) M (Normal Range) | (3) M (Test Data) | (4) $\sigma$ (Normal Range) | (5) $\sigma$ (Test Data) | (6) M/M$_\pi$ (Normal Range) | (7) M/M$_\pi$ (Test Data) | (8) $\sigma/\sigma_\pi$ (Normal Range) | (9) $\sigma/\sigma_\pi$ (Test Data) |
|---|---|---|---|---|---|---|---|---|
| P1-P2 | 120.9 ± 30.6 | 128.2 | 8.4 ± 4.7 | 3.7 | 0.14 ± 0.03 | 0.10 | 0.224 ± 0.101 | 0.040 |
| P1-P | 61.3 ± 16.0 | 66.1 | 4.1 ± 2.5 | 1.7 | 0.07 ± 0.02 | 0.05 | 0.110 ± 0.053 | 0.018 |
| P-P2 | 59.6 ± 14.7 | 62.1 | 4.5 ± 2.3 | 2.3 | 0.07 ± 0.01 | 0.05 | 0.120 ± 0.049 | 0.025 |
| P2-Q | 51.2 ± 25.4 | 41.5 | 5.3 ± 2.5 | 3.5 | 0.06 ± 0.02 | 0.03 | 0.143 ± 0.043 | 0.037 |
| Q-S | 70.8 ± 26.2 | 82.1 | 2.7 ± 1.1 | 1.2 | 0.08 ± 0.03 | 0.05 | 0.072 ± 0.024 | 0.013 |
| Q-R | 30.3 ± 4.7 | 34.4 | 2.7 ± 2.2 | 0.2 | 0.04 ± 0.00 | 0.03 | 0.073 ± 0.046 | 0.002 |
| Q-T2 | 374.1 ± 45.0 | 435.5 | 4.4 ± 1.5 | 2.4 | 0.45 ± 0.04 | 0.34 | 0.118 ± 0.032 | 0.026 |
| Q-T | 291.7 ± 34.8 | 346.2 | 2.7 ± 1.0 | 1.6 | 0.35 ± 0.03 | 0.27 | 0.071 ± 0.022 | 0.017 |
| R-S | 40.4 ± 25.3 | 27.7 | 2.4 ± 1.5 | 1.2 | 0.05 ± 0.02 | 0.02 | 0.065 ± 0.031 | 0.013 |
| P-R | 141.1 ± 32.3 | 138.0 | 2.2 ± 1.2 | 2.1 | 0.17 ± 0.03 | 0.11 | 0.059 ± 0.026 | 0.023 |
| R-R | 837.0 ± 172.4 | 1264.8 | 37.4 ± 24.2 | 93.7 | 1.00 ± 0.00 | 1.00 | 1.000 ± 0.000 | 1.000 |
| R-T | 261.4 ± 35.1 | 311.9 | 1.6 ± 0.3 | 1.6 | 0.31 ± 0.03 | 0.25 | 0.047 ± 0.006 | 0.017 |
| S-T2 | 303.4 ± 47.7 | 373.5 | 4.0 ± 1.6 | 2.5 | 0.38 ± 0.05 | 0.30 | 0.106 ± 0.033 | 0.026 |
| T1-T2 | 167.6 ± 26.6 | 178.5 | 10.1 ± 4.8 | 3.0 | 0.20 ± 0.03 | 0.14 | 0.270 ± 0.105 | 0.033 |
| S-T1 | 121.6 ± 33.9 | 137.8 | 2.9 ± 1.3 | 5.9 | 0.15 ± 0.03 | 0.11 | 0.078 ± 0.027 | 0.063 |
| S-T | 221.0 ± 38.5 | 284.2 | 2.9 ± 0.8 | 1.8 | 0.26 ± 0.04 | 0.22 | 0.054 ± 0.017 | 0.018 |

On the basis of further tests performed by the inventor, it has been found that certain correlation coefficients may be evaluated for data gathered from different test subject, thereby complementing the above fingerprinting approach, and serving to further demonstrate its validity.

More particularly, and referring now to FIG. 13, there are shown two superimposed plots of M for two sets of intracycle intervals originating at Q. The plots are for a 46 year old male and a 35 year old female, both of whom were comparing the evaluated statistical parameters with reference values thereby to provide an indication of the state of the selected activity.

2. A method according to claim 1, wherein said step of observing includes the step of measuring the time period taken by each activity, and said step of evaluating includes the step of evaluating predetermined statistical parameters of the time periods of a selected activity in a selected number of the sequence of heart cycles.

3. A method according to claim 2, wherein said step of evaluating includes evaluating a first statistical parameter indicating the state of the selected activity at the time of performing said step of detecting, and said step of comparing includes comparing said evaluated first parameter with a reference range, and further includes the step of determining a relationship between said evaluated first statistical parameter and the reference range, thereby to also determine the physiological state of the mammal at the time of performing said step of detecting.

4. A method according to claim 3, wherein said step of evaluating also includes evaluating a second statistical parameter indicating a trend in the state of the selected activity, and said step of comparing also includes comparing said evaluated second parameter with a reference range, and further includes the step of determining a relationship between said evaluated second statistical parameter and the reference range, thereby to also determine the trend in the state of the selected activity.

5. A method according to claim 4, wherein said step of comparing further includes the step of providing a visual reference system which includes first visual indications corresponding to said reference range, including a plurality of reference axes, each corresponding to a different predetermined heart activity, and said step of determining a relationship includes the substeps of:
providing on said reference axes second visual indications corresponding to values of a predetermined statistical quantity for each said heart activity; and
visually comparing said second visual indications with said first visual indications, thereby to determine a relationship therebetween.

6. A method according to claim 5, wherein the reference system is a multi-axis reference system which has a plurality of axes radiating from an origin, wherein each axis defines a scale on which is indicated a range of possible values of said predetermined statistical quantities corresponding for a predetermined heart activity, and herein the first visual indications of the reference system are closed-shape line markings provided concentrically about the origin, thereby to define at least first and second reference regions, wherein visual indications within said first region indicate a first state of health of the heart of the mammal, and visual indications within said second region indicate a second state of heath of the heart of the mammal, different from said first state of health, and wherein said step of comparing said second visual indications with said first visual indications comprises determining where said second visual indications fall relative to said reference regions, thereby to visually determine the state of health of the heart of the mammal.

7. A method according to claim 6, wherein said step of provided a reference system comprises the following steps:
detecting periodic activity of internal heart organs in a sequence of heart cycles for a statistically representative number of subjects each having a similar physiological conditions;
observing a plurality of predetermined physical quantities each characteristic of a known heart activity;
evaluating selected statistical parameters of each of the predetermined physical quantities for a selected number of the sequence of heart cycles for each of the subjects;
determining minimum and maximum values for each of said selected statistical parameters, thereby to define a range of values for each said parameter for subjects having said physiological condition; and
plotting said range of values on said multi-axis reference system, thereby to indicate visually said minimum and maximum values for each said statistical parameter for each said heart activity.

8. A method according to claim 1, wherein said step of detecting periodic activity of internal heart organs includes:
sensing at the body surface of a mammal electrical potentials produced by heart activity thereof, during a predetermined minimum number of consecutive heart cycles;
providing an analog output signal corresponding to the sensed electrical potentials;
sampling said analog output signal at a high frequency sampling rate, so as to convert said analog output signal into digital signals which retain substantially all the information contained in the sensed electrical potentials;
storing said digital signals signals as input data in an initial input file; and
providing a high resolution output waveform corresponding to said input data in which substantially only information concerning heart activity is represented, which includes:
determining waveform characteristic points,
superposing said characteristic points on said output waveform, thereby to divide said waveform into a plurality of waveform cycles each corresponding to a single heart cycle, and also so as to divide each said waveform into a plurality of waveform portions each being located between two selected characteristic points, and being defined by a plurality of points;
selecting a waveform portion alignment point;
aligning with each other all corresponding portions of said waveform cycles along said selected alignment point; and
averaging the ordinates of all said points of all said aligned waveform portions, thereby to reduce the effects of non-useful information and thus to produce a signal waveform which is characteristic of the heart activity of the mammal.

9. A method according to claim 8, wherein said step of sampling is performed at a rate of greater that 500 times per second.

10. A method according to claim 9, wherein said step of sampling is performed at a rate of at least 750 times per second.

11. A method according to claim 10, wherein said step of sampling is performed at a rate of at least 5,290 times per second.

12. A method according to claim 8, wherein said step of providing a high resolution output waveform includes the step of visually displaying said waveform.

13. A method according to claim 12, wherein said step of visually displaying includes provision of visual indications corresponding to activity of individual internal heart organs.

14. A method according to claim 8, wherein said step of determining waveform characteristic points includes determining Q, R and S points, and includes the following sub-steps:
identifying maxima on the output waveform, thereby to determine R peaks of all intervals thereof;
determining a minimum point Q immediately preceding the R peak; and approximating a minimum point S' immediately succeeding the R peak.

15. A method according to claim 14, wherein said step of determining the minimum point Q includes the sub-step of obtaining a first derivation of the output waveform along the portion thereof immediately preceding R, and said step of approximating the S minimum points comprises the sub-step of obtaining a first derivative of the waveform along the portion thereof immediately succeeding R.

16. A method according to claim 14, and also including the steps, after said step of approximating, of:

determining a P wave portion preceding the Q point and bounded by points P1 and P2, and determining a T wave portion succeeding the S point and bounded by points T1 and T2.

17. A method according to claim 16, wherein said step of determining a P wave portion includes approximating the P-wave by applying the exponential expression $$Y_p(x) = A_p e^{-\lambda x^2}$$

in which $Y_p$ represents the ordinates of the points along the P-wave, $A_p$ is the maximum of said exponential expression and is located at the midpoint between the points P1 and P2, and $\lambda$ is determined from the lower of the sum of the mean square deviations between the ordinates of the waveform, and of the sum of said exponential expression; and said step of determining a T wave comprises approximating the T wave by applying the exponential expression $$Y_t(x) = A_p e^{-\lambda x^2},$$

and wherein, in said exponential expression, $Y_t$ represents the ordinates of the points along the T wave, $A_t$ is the maximum of said exponential expression and is located at the midpoint between the pints T1 and T2, and $\lambda$ is determined from the lower of the sum of the mean square deviations between the ordinates of the waveform, and of the sum of said exponential expression.

18. A method according to claim 17, wherein, said step of determining the P wave also includes the steps of:

determining the distance between P1 and P2 by applying the function $k(\lambda, A) \times \lambda$, and determining the locations of points P1 and P2;

and wherein, said step of determining the T wave also includes the steps of:

determining the distance between T1 and T2 by applying the function $k(\lambda A) \times \lambda$, and determining the locations of points T1 and T2.

19. A method according to claim 18, said step of determining the P wave also includes the step of performing a third order polynomial approximation of the P wave, wherein P1 and P2 are two of the roots of said approximation, and the third root thereof is P, and said step of determining the T wave also includes the step of performing a third order polynomial approximation of the T wave, wherein T1 and T2 are two of the roots of said approximation, and the third root thereof is T.

20. A method according to claim 19, and further including the following steps:

constructing a seventh order polynomial for the Q→T1 waveform portion;

performing a second approximation of the point S", and determining the point S", as the root of said seventh order polynomial immediately succeeding R.

21. A system for providing an indication of the physiological state of the heart of a mammal which includes:

apparatus for detecting periodic activity of internal heart organs in a sequence of heart cycles and for providing output signals corresponding thereto;

apparatus associated with said apparatus for detecting, for receiving said output signals and for determining in accordance therewith a predetermined physical quantity characteristic of an activity;

apparatus for evaluating predetermined statistical parameters of the predetermined physical quantity for a selected number of the sequence of heart cycles; and apparatus for comparing the evaluated statistical parameters with reference values thereby to provide an indication of the state of the selected activity.

22. A system according to claim 21, wherein said apparatus for receiving and determining includes apparatus for determining the time period taken by each activity, and said apparatus for evaluating includes apparatus for evaluating predetermined statistical parameters of the time periods of a selected activity in a selected number of the sequence of heart cycles.

23. A system according to claim 22 wherein said apparatus for evaluating includes apparatus for evaluating a first statistical parameter indicating the state of the selected activity during operation of said apparatus for detecting, and said apparatus for comparing includes;

apparatus for comparing the evaluated first parameter with a reference range corresponding to a state of health of the mammal, and apparatus for visually displaying said reference range and the evaluated first parameter, thereby to provide an indication of the state of health of the mammal.

24. A system according to claim 23, wherein said apparatus for evaluating also includes apparatus for evaluating a second statistical parameter indicating a trend in the state of the selected activity, and said apparatus for comparing includes;

apparatus for comparing the evaluated second parameter with a reference range corresponding to a trend in the state of health of heart of the mammal, and apparatus for visually displaying said reference range and the evaluated second parameter, thereby to provide an indication of a trend in the state of health of the heart of the mammal.

25. A system according to claim 22, wherein said apparatus for comparing includes, a multi-axis visual reference system which includes:

a plurality of axes radiating from an origin, wherein each axis defines a scale on which is indicated a range of possible values of said predetermined statistical quantities corresponding to a predetermined heart activity, a plurality of closed-shape line markings provided concentrically about said origin, thereby to define at least first and second reference regions, wherein visual indications within said first region indicate a first state of health of the heart of the mammal, and visual indications within said second region indicate a second state of health of the heart of the mammal, different from said first state of health.

26. A system according to claim 22, wherein said apparatus for detecting period activity includes:

electrode apparatus for sensing at the body surface of a mammal electrical potentials produced by heart activity thereof, during a predetermined minimum number of consecutive heart cycles, and for providing an analog output signal corresponding to the sensed electrical potentials;

sampling apparatus for sampling said analog output signal at a high frequency sampling rate, and for converting said analog output signal into digital signals which retain substantially all the information contained in the sensed electrical potentials;

memory apparatus for storing said digital signals as input data in an initial input file; and processing apparatus for providing a high resolution output waveform corresponding to said input data in which substantially only information concerning heart activity is represented; and which includes:

apparatus for determining waveform characteristic points, apparatus for superposing said characteristic points on said output waveform, thereby to divide said waveform into a plurality of waveform cycles each corresponding to a single heart cycle, and also so as to divide each said waveform cycle into a plurality of waveform portions each being located between two selected characteristic points, and being defined by a plurality of points;

apparatus for selecting a waveform portion alignment point;

apparatus for aligning with each other all corresponding portions of said waveform cycles along said selected alignment point; and apparatus for averaging the ordinates of all said points of all said aligned waveform portions, thereby to reduce the effects of non-useful information and thus to produce a single waveform which is characteristic of the heart activity of the mammal.

27. A system according to claim 26, wherein said sampling apparatus is operative to sample said analog output signal at a rate exceeding 500 times per second.

28. A system according to claim 27, and also including apparatus associated with said processing apparatus, for visually displaying said waveform.

29. A system according to claim 28, wherein said display apparatus includes apparatus for displaying visual indications corresponding to activity of individual internal heart organs.

30. A system according to claim 27, wherein said processing apparatus further comprises apparatus for stabilizing said output waveform, which includes:

adaptive high pass filtering apparatus for the digital signals at a threshold preselected in accordance with the heart rate of a subject so as to provide an adjusted waveform;

apparatus for determining an ordinates histogram of said adjusted waveform;

apparatus for determining the modal value of said histogram;

apparatus for determining a baseline for said adjusted waveform corresponding to said modal value of said histogram; and apparatus for combining said baseline and said adjusted waveform so as to provide a stabilized waveform.

31. A system according to claim 26, wherein said sampling apparatus is operative to sample said analog output signal at a rate exceeding 750 times per second.

32. A system according to claim 26, wherein said sampling apparatus is operative to sample said analog output signal at a rate exceeding 5,290 times per second.

33. A multi-axis visual reference system for indicating the state of health of the heart of a mammal, which includes:

a plurality of axes radiating from an origin, wherein each axis defines a scale on which is indicated a range of possible values of a predetermined statistical quantity corresponding to a predetermined heart activity, and a plurality of closed-shape line markings provided concentrically about said origin, thereby to define at least first and second reference regions, wherein visual indications within said first region indicate a first state of health of the heart of the mammal, and visual indications within said second region indicate a second state of health of the heart of the mammal, different from said first state of health.

34. A reference system according to claim 33, wherein said first region indicates a first range of values defining a statistically determined healthy range for the predetermined heart activity, and said second region indicates a second range of values beyond said first range, thereby to indicate an unhealthy range vis-a-vis the predetermined activity.

35. A reference system according to claim 34, and also comprising a third region which indicates a third range of values defining a statistically determined diseased range for the predetermined heart activity, wherein said second region indicates a range of values between said first and third ranges, thereby to indicate a statistically determined intermediate health range for the predetermined heart activity.

36. A reference system according to claim 34, wherein said visual indications within said at least first and second reference regions correspond to the state of health of the heart of the mammal at the time at which heart activity of the mammal is sampled.

37. A reference system according to claim 34, wherein said visual indications within said at least first and second reference regions correspond to a statistically determined trend in the state of health of the heart of the mammal subsequent to the time at which heart activity of the mammal is sampled.

* * * * *

UNITED STATES PATENT AND TRADEMARK OFFICE
CERTIFICATE OF CORRECTION

PATENT NO. : 6,246,903 B1
DATED : June 12, 2001
INVENTOR(S) : Solomon Kletskin

It is certified that error appears in the above-identified patent and that said Letters Patent is hereby corrected as shown below:

Column 16,
Line 25, change "methods" to -- method --;

Column 17,
Line 42, change "herein" to -- wherein --;
Line 57, change "provided" to -- providing --;
Line 61, change "conditions" to -- condition --;

Column 18,
Line 33, after "waveform" (first occurrence) insert -- cycle --;

Column 19,
Line 55, change "k($\lambda$A)x$\lambda$" to -- k($\lambda$,A)x$\lambda$ --.

Signed and Sealed this

Second Day of August, 2005

JON W. DUDAS
*Director of the United States Patent and Trademark Office*